(12) United States Patent
Lippard et al.

(10) Patent No.: US 9,593,139 B2
(45) Date of Patent: Mar. 14, 2017

(54) COMPOSITIONS, METHODS, AND KITS COMPRISING PLATINUM COMPOUNDS ASSOCIATED WITH A LIGAND COMPRISING A TARGETING MOIETY

(71) Applicant: Massachusetts Institute of Technology, Cambridge, MA (US)

(72) Inventors: Stephen J. Lippard, Cambridge, MA (US); Justin J. Wilson, Cambridge, MA (US); Robert John Radford, Cambridge, MA (US); Maria R. Chan, Cambridge, MA (US); Daniel Y. Zhang, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 198 days.

(21) Appl. No.: 14/245,360

(22) Filed: Apr. 4, 2014

(65) Prior Publication Data
US 2014/0343139 A1 Nov. 20, 2014

Related U.S. Application Data

(60) Provisional application No. 61/808,874, filed on Apr. 5, 2013.

(51) Int. Cl.
*C07F 15/00* (2006.01)
(52) U.S. Cl.
CPC ................ *C07F 15/0093* (2013.01)
(58) Field of Classification Search
CPC .................................................. C07F 15/0093
See application file for complete search history.

(56) References Cited

U.S. PATENT DOCUMENTS

| | | | |
|---|---|---|---|
| 4,843,161 A | 6/1989 | Lippard et al. | |
| 5,244,919 A | 9/1993 | Abrams et al. | |
| 6,806,289 B1 | 10/2004 | Lippard et al. | |
| 7,138,520 B2 | 11/2006 | Lippard et al. | |
| 7,232,919 B2 | 6/2007 | Lal | |
| 8,729,286 B2 * | 5/2014 | Lippard .............. | C07F 15/0093 424/649 |
| 9,034,862 B2 | 5/2015 | Lippard et al. | |
| 9,133,225 B2 | 9/2015 | Lippard et al. | |
| 2004/0235712 A1 | 11/2004 | Lippard et al. | |
| 2005/0090478 A1 | 4/2005 | Barenholz et al. | |
| 2007/0082882 A1 | 4/2007 | Farrell | |
| 2007/0104654 A1 | 5/2007 | Hsieh et al. | |
| 2007/0154398 A1 | 7/2007 | Wang et al. | |
| 2010/0330197 A1 | 12/2010 | Higashiguchi et al. | |
| 2011/0257261 A1 | 10/2011 | Lippard et al. | |
| 2011/0300219 A1 | 12/2011 | Lippard et al. | |
| 2013/0029959 A1 | 1/2013 | Lippard et al. | |
| 2013/0303606 A1 | 11/2013 | Lippard et al. | |
| 2014/0274988 A1 | 9/2014 | Lippard et al. | |

FOREIGN PATENT DOCUMENTS

| | | |
|---|---|---|
| DE | 19623746 A1 | 12/1997 |
| EP | 0 199 524 B1 | 2/1992 |
| EP | 0 679 656 A1 | 11/1995 |
| WO | WO 2005/092298 A1 | 10/2005 |
| WO | WO 2006/108276 A1 | 10/2006 |
| WO | WO 2007/021852 A2 | 2/2007 |
| WO | WO 2007/124314 A2 | 11/2007 |
| WO | WO 2007/133807 A2 | 11/2007 |
| WO | WO 2008/121949 A1 | 10/2008 |
| WO | WO 2009/032172 A2 | 3/2009 |
| WO | WO 2010/047765 A2 | 4/2010 |
| WO | WO 2010/150036 A1 | 12/2010 |
| WO | WO 2012/177935 A1 | 12/2012 |

OTHER PUBLICATIONS

Okeya et al. "Reactions of the Bis(β-diketonato)platinum(II) Complexes with Various Nitrogen Bases" Bulletin of the Chemical Society of Japan, 1982, vol. 55, pp. 1460-1466.*
Invitation to Pay Additional Fees for PCT/US2014/33011 mailed Aug. 22, 2014.
International Search Report and Written Opinon for PCT/US2014/33011 mailed Oct. 31, 2014.
Abramkin et al., Solid-phase synthesis of oxaliplatin-TAT peptide bioconjugates. Dalton. Trans. Mar. 14, 2012;41(10):3001-5. doi: 10.1039/c2dt12024k. Epub Jan. 27, 2012.
Al-Allaf et al., Platinum(II) and palladium(II) complexes analogous to oxaliplatin with different cyclohexyldicarboxylate isomeric anions and their in vitro antitumour activity. Structural elucidation of [Pt(C204)(cis-dach)]. Transition Metal Chemistry. 2003;28: 717-21.
Anderson et al., Alpha-TEA plus cisplatin reduces human cisplatin-resistant ovarian cancer cell tumor burden and metastasis. Exp Biol Med (Maywood). Dec. 2004;229(11):1169-76.
Ang et al., Transcription inhibition by platinum-DNA cross-links in live mammalian cells. J Am.Chem Soc. Jun. 2, 2010;132(21):7429-35. doi: 10.1021/ja101495v.
Barragan et al., Solid-phase synthesis and DNA binding studies of dichloroplatinum(II) conjugates of octreotide as new anticancer drugs. Chem Commun (Camb) Aug. 21, 2009;(31):4705-7. doi: 10.1039/b909698a. Epub Jun. 22, 2009.
Barragan et al., Somatostatin subtype-2 receptor-targeted metal-based anticancer complexes. Bioconjug Chem. Sep. 19, 2012;23(9):1838-55. Epub Aug. 20, 2012.
Bauer et al., Monofunctional platinum amine complexes destabilize DNA significantly. Eur J. Biochem. Sep. 1, 1998;256(2):253-60.
Borrelli et al., A molecular carrier to transport and deliver cisplatin into endometrial cancer cells. Chem Biol Drug Des. Jul. 2012;80(1):9-16. doi: 10.1111/j.1747-0285.2012.01337.x. Epub Apr 27, 2012.

(Continued)

*Primary Examiner* — Joseph Kosack
(74) *Attorney, Agent, or Firm* — Wolf, Greenfield & Sacks, P.C.

(57) ABSTRACT

Compositions, kits, and methods for treatment of cancers are generally provided. In some embodiments, the compositions, kits, and methods comprise a platinum (e.g., Pt(II) or Pt(IV)) compound associated with a ligand (e.g., a beta-diketonate ligand) comprising a targeting moiety. Methods of synthesizing platinum (e.g., Pt(II) or Pt(IV)) compounds associated with a ligand comprising a targeting moiety are also provided.

29 Claims, 11 Drawing Sheets

(56) References Cited

OTHER PUBLICATIONS

Cohen et al., Binding of cis- and trans-dichlorodiammineplatinum(II) to DNA: evidence for unwinding and shortening of the double helix. Science. Mar. 9, 1979;203(4384):1014-6.

Comess et al., Replication inhibition and translesion synthesis on templates containing site-specifically placed cis-diamminedichloroplatinum(II) DNA adducts. Biochemistry. Apr. 28, 1992;31(16):3975-90.

Costello et al., Evidence for changes in RREB-1, ZIP3, and Zinc in the early development of pancreatic adenocarcinoma. J Gastrointest Cancer. Dec. 2012;43(4):570-8. doi: 10.1007/s12029-012-9378-1.

Cullen et al., Mitochondria as a critical target of the chemotheraputic agent cisplatin in head and neck cancer. J Bioenerg Biomembr. Feb. 2007;39(1):43-50.

Damian et al., Synthesis and DNA Interaction of Platinum Complex/Peptide Chimera as Potential Drug Candidates. Eur J Org Chem. Nov. 2010; 2010(32): 6161-70.

Deng et al., Crystallographic characterization of trans-bis(acetato)(1,1-cyclobutanedicarboxylato)ethylenediamineplatinum(IV) trihydrate. Inorganica Chimica Acta. Feb. 1, 1993;204(1):35-38.

De Pascali et al., First Examples of β-Diketonate Platinum(II) Complexes with Sulfoxide Ligands. Eur Journal of Inorg Chem. Feb. 2005; (4): 788-96.

De Pascali et al., Mutagenic Tests Confirm That New Acetylacetonate Pt(II) Complexes Induce Apoptosis in Cancer Cells Interacting with Nongenomic Biological Targets. Met Based Drugs. 2011;2011:763436. doi: 10.1155/2011/763436. Epub Apr. 10, 2011.

DeSoize et al., Particular aspects of platinum compounds used at present in cancer treatment. Crit Rev Oncol Hematol. Jun. 2002;42(3):317-25.

Dhar et al., Current Status and Mechanism of Action of Platinum-Based Anticancer Drugs. Bioinorganic Medicinal Chemistry, Enzo Alessio, Ed. Wi-ley-VCH Verlag GmbH & Co. KgaA. Weinheim, Germany, Chapter 3. 2010:79-95.

Dhar et al., Mitaplatin, a potent fusion of cisplatin and the orphan drug dichloroacetate. Proc Natl Acad Sci U S A. Dec. 29, 2009;106(52):22199-204. doi: 10.1073/pnas.0912276106. Epub Dec. 10, 2009.

Dhar et al., Polyvalent oligonucleotide gold nanoparticle conjugates as delivery vehicles for platinum(IV) warheads. J Am Chem Soc. Oct. 21, 2009;131(41):14652-3. doi: 10.1021/ja9071282.

Dhar et al., Targeted delivery of cisplatin to prostate cancer cells by aptamer functionalized Pt(IV) prodrug-PLGA-PEG nanoparticles. Proc Natl Acad Sci U S A. Nov. 11, 2008;105(45):17356-61. doi: 10.1073/pnas.0809154105. Epub Oct. 31, 2008.

Dhar et al., Targeted single-wall carbon nanotube-mediated Pt(IV) prodrug delivery using folate as a homing device. J Am Chem Soc. Aug. 27, 2008;130(34):11467-76. doi: 10.1021/ja803036e. Epub Jul. 29, 2008.

Dodd et al., Peptide nucleic acid Pt(II) conjugates: a preliminary study of antisense effects in Xenopus laevis. Nucleosides Nucleotides Nucleic Acids. Apr. 2011;30(4):257-63. doi: 10.1080/15257770.2011.580290.

Dorwald, Side Reactions in Organic Synthesis: A Guide to Successful Design. Wiley VCH GmbH & Co. KGaA. 2005. pp. 1-15.

Flazell et al., Soluble single-walled carbon nanotubes as longboat delivery systems for platinum(IV) anticancer drug design. J Am Chem Soc. Jul. 11, 2007;129(27):8438-9. Epub Jun. 15, 2007.

Fink et al., In vitro and in vivo resistance to cisplatin in cells that have lost DNA mismatch repair. Cancer Res. May 15, 1997;57(10):1841-5.

Fink et al., The role of DNA mismatch repair in platinum drug resistance. Cancer Res. Nov. 1, 1996;56(21):4881-6.

Fonseca et al., Recent advances in the use of cell-penetrating peptides for medical and biological applications. Adv Drug Deliv Rev. Sep. 30, 2009;61(11):953-64. doi: 10.1016/j.addr.2009.06.001. Epub Jun. 16, 2009.

Fonseca et al., Rerouting chlorambucil to mitochondria combats drug deactivation and resistance in cancer cells. Chem Biol. Apr. 22, 2011;18(4):445-53. doi: 10.1016/j.chembiol.2011.02.010.

Fulda et al., Targeting mitochondria for cancer therapy. Nat Rev Drug Discov. Jun. 2010;9(6):447-64. doi: 10.1038/nrd3137. Epub May 14, 2010.

Galanski et al., Update of the preclinical situation of anticancer platinum complexes: novel design strategies and innovative analytical approaches. Curr Med Chem. 2005;12(18):2075-94.

Gaviglio et al., Synthesis and in vitro cytotoxicity of cis,cis,trans-diamminedichloridodisuccinatoplatinum(IV)-peptide bioconjugates. Metallomics. Mar. 2012;4(3):260-6. doi: 10.1039/c2mt00171c. Epub Feb. 7, 2012.

Giandomenico et al., Carboxylation of Kinetically Inert Platinum(IV) Hydroxy Complexes. An Entr.acte.ee into Orally Active Platinum(IV) Antitumor Agents. Inorg Chem. Mar. 1995;34(5):1015-21. doi: 10.1021/ic00109a004.

Gill et al., Synthese, kinetics and mechanism of formation of polynuclear hydroxo-bridged complexes of (trans-1,2-diaminocyclohexane)platinum(II). J Am Chem Soc. 1982;104:4598-604.

Graf et al., Platinum(IV)-chlorotoxin (CTX) conjugates for targeting cancer cells. J Inorg Biochem. May 2012;110:58-63. doi: 10.1016/j.jinorgbio.2012.02.012. Epub Feb. 23, 2012.

Hall et al., Basis for design and development of platinum(IV) anticancer complexes. J Med Chem. Jul. 26, 2007;50(15):3403-11. Epub Jun. 28, 2007.

Hall et al. Platinum(IV) antitumour compounds: their bioinorganic chemistry. Coord Chem Rev. 2002; 232:49-67.

He et al., Steroid hormones induce HMG1 overexpression and sensitize breast cancer cells to cisplatin and carboplatin. Proc Natl Acad Sci U S A. May 23, 2000;97(11):5768-72.

Hoeschele et al., Synthesis and characterization of diastereomeric (substituted iminodiacetato)(1,2-diaminocyclohexane)platinum(II) complexess. Inorganic Chemistry. 1988;27:4106-13.

Hollis et al., Chemical and biological properties of a new series of cis-diammineplatinum(II) antitumor agents containing three nitrogen donors: cis-[Pt(NH3)2(N-donor)Cl]+. J Med Chem. Jan. 1989;32(1):128-36.

Hollis et al., Mechanistic studies of a novel class of trisubstituted platinum(II) antitumor agents. Cancer Res. Apr. 1, 1991;51(7):1866-75.

Hollis et al., Synthesis and Structures of Platinum(III) Complexes of α-Pyridone, [X(NH3)2Pt(C5H4NO)2Pt(NH3)2X](NO3)2*nH2O (X- = Cl-, NO2-, Br-). Inorg Chem. 1983;22:3637-44.

Horton et al., Mitochondria-penetrating peptides. Chem Biol. Apr. 2008;15(4):375-82. doi: 10.1016/j.chembiol.2008.03.015.

Horton et al., Tuning the activity of mitochondria-penetrating peptides for delivery or disruption. Chembiochem. Feb. 13, 2012;13(3):476-85. doi: 10.1002/cbic.201100415. Epub Jan. 11, 2012.

Howe-Grant et al., Aqueous Platinum (II) Chemistry; Binding to Biological Molecules. Metal Ions in Biological Systems. Sigel et al., eds. 1980;11:63-125.

Isonishi et al., Mitochondria in platinum resistant cells. Hum Cell. Sep. 2001;14(3):203-10.

Ivanov et al., Biological activity of platinum (II) complexes of the triamine type as a function of their composition and structure. Izv Akad Nauk Ser Biol. May-Jun. 1995;(3):281-90. English abstract found on p. 290.

Jamieson et al., Structure, Recognition, and Processing of Cisplatin-DNA Adducts. Chem Rev. 1999;99:2467-98.

Tin et al., Platinum(II) triammine antitumour complexes: structure-activity relationship with guanosine 5'-monophosphate (5'-GMP). Inorganica Chimica Acta. 2005;358:677-86.

Jung et al., RNA polymerase II blockage by cisplatin-damaged DNA. Stability and polyubiquitylation of stalled polymerase. J Biol Chem. Jan. 20, 2006;281(3):1361-70. Epub Nov. 7, 2005.

Kapp et al., Dinuclear alkylamine platinum(II) complexes of [1,2-bis(4- fluorophenyl)ethylenediamine]platinum(II): influence of endocytosis and copper and organic cation transport systems on cellular uptake. ChemMedChem. May 2006;1(5):560-4.

Kartalou et al., Mechanisms of resistance to cisplatin. Mutat Res. Jul. 1, 2001;478(1-2):23-43.

(56) References Cited

OTHER PUBLICATIONS

Kawai et al., Synthesis, structure and antitumor activity of a new water-soluble platinum complex, (1R,2R-cyclohexanediamine-N,N')[2-hydroxy-4-oxo-2-pentenoato(2+)-O2] platinum(II). Chem Pharm Bull (Tokyo). Feb. 1993;41(2):357-61.
Keck et al., Unwinding of supercoiled DNA by platinum-ethidium and related complexes. J Am Chem Soc. 1992;114:3386-90.
Kelland et al., the resurgence of platinum-based cancer chemotherapy. Nat Rev Cancer. Aug. 2007;7(8):573-84. Epub Jul. 12, 2007.
Kidani et al., Antitumor activity of 1,2-diaminocyclohexane--platinum complexes against sarcoma-180 ascites form. J Med Chem. Dec. 1978;21(12):1315-8.
Kostova, Platinum complexes as anticancer agents. Recent Pat Anticancer Drug Discov. Jan. 2006;1(1):1-22.
Kujoth et al., Mitochondrial DNA mutations, oxidative stress, and apoptosis in mammalian aging. Science. Jul. 15, 2005;309(5733):481-4.
Lebwohl et al., Clinical development of platinum complexes in cancer therapy: an historical perspective and an update. Eur J Cancer. Sep. 1998;34(10):1522-34.
Lee et al., Transcription-coupled and DNA damage-dependent ubiquitination of RNA polymerase II in vitro. Proc Natl Acad Sci U S A. Apr. 2, 2002;99(7):4239-44. Epub Mar. 19, 2002.
Lempers et al., The new antitumor compound, cis-[Pt(NH3)2(4-methylpyridine)Cl]Cl, does not form N7,N7-d(GpG) chelates with DNA. An unexpected preference for platinum binding at the 5'G in d(GpG). J Inorg Biochem. Sep. 1990;40(1):23-35.
Lippard , Chemical synthesis: the art of chemistry. Nature. Apr. 11, 2002;416(6881):587.
Lovejoy et al., cis-Diammine(pyridine)chloroplatinum(II), a monofunctional platinum(II) antitumor agent: Uptake, structure, function, and prospects. Proc Natl Acad Sci U S A. Jul. 1, 2008;105(26):8902-7. doi: 10.1073/pnas.0803441105. Epub Jun. 25, 2008.
Lovejoy et al., Non-traditional platinum compounds for improved accumulation, oral bioavailability, and tumor targeting. Dalton Trans. Dec. 28, 2009;(48):10651-9. doi: 10.1039/b913896j. Epub Oct. 1, 2009.
Lovejoy et al., Spectrum of cellular responses to pyriplatin, a monofunctional cationic antineoplastic platinum(II) compound, in human cancer cells. Mol Cancer Ther. Sep. 2011;10(9):1709-19. doi: 10.1158/1535-7163.MCT-11-0250. Epub Jul. 12, 2011.
Malafa et al., Vitamin E succinate promotes breast cancer tumor dormancy. J Surg Res. Sep. 2000;93(1):163-70.
Malafa et al., Vitamin E succinate suppresses prostate tumor growth by inducing apoptosis. Int J Cancer. May 15, 2006;118(10):2441-7.
Margiotta et al., Sterically hindered complexes of platinum(II) with planar heterocyclic nitrogen donors. A novel complex with 1-methyl-cytosine has a spectrum of activity different from cisplatin and is able of overcoming acquired cisplatin resistance. J Inorg Biochem. Nov. 2006;100(11):1849-57. Epub Aug. 3, 2006.
Martin et al., Do structurally similar molecules have similar biological activity? J Med Chem. Sep. 12, 2002;45(19):4350-8.
Misset et al., Oxaliplatin clinical activity: a review. Crit Rev Oncol Hematol. Aug. 2000;35(2):75-93.
Mourtada et al., Re-directing an alkylating agent to mitochondria alters drug target and cell death mechanism. PLoS One. Apr. 9, 2013;8(4):e60253. doi: 10.1371/journal.pone.0060253. Print 2013.
Mukhopadhyay et al., Conjugated platinum(IV)-peptide complexes for targeting angiogenic tumor vasculature. Bioconjug Chem. Jan. 2008;19(1):39-49. Epub Sep. 11, 2007.
Muscella et al., [Pt(O,O'-acac)(gamma-acac)(DMS)], a new Pt compound exerting fast cytotoxicity in MCF-7 breast cancer cells via the mitochondrial apoptotic pathway. Br J Pharmacol. Jan. 2008;153(1):34-49. Epub Nov. 19, 2007.
Muscella et al., New platinum(II) complexes containing both an O,O'-chelated acetylacetonate ligand and a sulfur ligand in the platinum coordination sphere induce apoptosis in HeLa cervical carcinoma cells. Biochem Pharmacol. Jun. 30, 2007;74(1):28-40. Epub Mar. 31, 2007.
Muscella et al., Sublethal concentrations of the platinum(II) complex [Pt(O,O'-acac)(gammaacac)(DMS)] alter the motility and induce anoikis in MCF-7 cells. Br J Pharmacol. Jul. 2010;160(6):1362-77. doi: 10.1111/j.1476-5381.2010.00782.x.
Ndinguri et al., Peptide targeting of platinum anti-cancer drugs. Bioconjug Chem. Oct. 21, 2009;20(10):1869-78. doi: 10.1021/bc900065r. Epub Sep. 23, 2009.
Neuzil et al., alpha-tocopheryl succinate-induced apoptosis in Jurkat T cells involves caspase-3 activation, and both lysosomal and mitochondrial destabilisation. FEBS Lett. Feb. 26, 1999;445(23):295-300.
Neuzil et al., Selective cancer cell killing by alpha-tocopheryl succinate. Br J Cancer. Jan. 5, 2001;84(1):87-9.
Neuzil, Vitamin E succinate and cancer treatment: a vitamin E prototype for selective antitumour activity. Br J Cancer. Nov. 17, 2003;89(10):1822-6.
Osol [Editor]. "Chapter 27: Structure-Activity Relationship and Drug Design". Remington's Pharmaceutical Sciences (Sixteenth Edition). Mack Publishing. 1980. pp. 420-435.
Page et al., Effect of the diaminocyclohexane carrier ligand on platinum adduct formation, repair, and lethality. Biochemistry. Jan. 30, 1990;29(4):1016-24.
Park et al., Phenanthriplatin, a monofunctional DNA-binding platinum anticancer drug candidate with unusual potency and cellular activity profile. Proc Natl Acad Sci U S A. Jul. 24, 2012;109(30):11987-92. doi: 10.1073/pnas.1207670109. Epub Jul. 6, 2012.
Peer et al., Nanocarriers as an emerging platform for cancer therapy. Nat Nanotechnol. Dec. 2007;2(12):751-60. doi: 10.1038/nnano.2007.387.
Perez et al., Current status of the development of trans-platinum antitumor drugs. Crit Rev Oncol Hematol. Aug. 2000;35(2):109-20.
Pinto et al., Binding of the antitumor drug cis-diamminedichloroplatinum(II) (cisplatin) to DNA. Biochim Biophys Acta. 1985;780(3):167-80.
Portney et al., Nano-oncology: drug delivery, imaging, and sensing. Anal Bioanal Chem. Feb. 2006;384(3):620-30. Epub Jan. 27, 2006.
Quin et al., Vitamin E succinate decreases lung cancer tumor growth in mice. J Surg Res. Aug. 2005;127(2): 139-43.
Rabik et al., Molecular mechanisms of resistance and toxicity associated with platinating agents. Cancer Treat Rev. Feb. 2007;33(1):9-23. Epub Nov. 3, 2006.
Reardon et al., Efficient nucleotide excision repair of cisplatin, oxaliplatin, and Bis-aceto-ammine-dichloro-cyclohexylamine-platinum(IV) (JM216) platinum intrastrand DNA diadducts. Cancer Res. Aug. 15, 1999;59(16):3968-71.
Reardon et al., Purification and characterization of *Escherichia coli* and human nucleotide excision repair enzyme systems. Methods Enzymol. 2006;408:189-213.
Robillard et al. Solid-phase synthesis of peptide-platinum complexes using platinum-chelating building blocks derived from amino acids. New J Chem. 2005. 29: 220-5.
Robillard et al., Automated parallel solid-phase synthesis and anticancer screening of a library of peptide-tethered platinum(II) complexes. J Comb Chem. Nov.-Dec. 2003;5(6):821-5.
Robillard et al., The First Solid-Phase Synthesis of a Peptide-Tethered Platinum(II) Complex. Angew Chem Int Ed Engl. Sep. 1, 2000;39(17):3096-3099.
Robillard et al., The interaction of peptide-tethered platinum(II) complexes with DNA. J Inorg Biochem. Aug. 1, 2003;96(2-3):331-8.
Sakai et al., A New One-Dimensional Platinum System Consisting of Carboxylate-Bridged cis-Diammineplatinum Dimers1. JACS. 1998;120:11353-63.
Schwartz et al., Preparation and antitumor evaluation of water-soluble derivatives of dichloro(1,2-diaminocyclohexane)platinum(II). Cancer Treat Rep. Nov. 1977;61(8):1519-25.

(56) References Cited

OTHER PUBLICATIONS

Shiau et al., alpha-Tocopheryl succinate induces apoptosis in prostate cancer cells in part through inhibition of Bcl-xL/Bcl-2 function. J Biol Chem. Apr. 28, 2006;281 (17): 11819-25. Epub Mar. 6, 2006.
Siddik, Cisplatin: mode of cytotoxic action and molecular basis of resistance. Oncogene. Oct. 20, 2003;22(47):7265-79.
Silverman et al., 2.4—A crystal structure of the asymmetric platinum complex [Pt(ammine)(cyclohexylamine)]2+ bound to a dodecamer DNA duplex. J Biol Chem. Dec. 20, 2002;277(51):49743-9. Epub Oct. 10, 2002.
Spingler et al., 2.4 A crystal structure of an oxaliplatin 1,2-d(GpG) intrastrand cross-link in a DNA dodecamer duplex. Inorg Chem. Oct. 22, 2001;40(22):5596-602.
Sporn et al., Chemoprevention of cancer. Carcinogenesis. Mar. 2000;21(3):525-30.
Stephen et al., The structural characterisation and elucidation of the electronic structure of the mononuclear Pt(III) complex [Pt([9]aneS3)2]3+ ([9]aneS3 = 1,4,7-trithiacyclononane). Chem Commun (Camb). Nov. 30, 2008;(44):5707-9. doi: 10.1039/b811645h. Epub Sep. 30, 2008.
Stewart et al., Cell-penetrating peptides as delivery vehicles for biology and medicine. Org Biomol Chem. Jul. 7, 2008;6(13):2242-55. doi: 10.1039/b719950c. Epub Apr. 15, 2008.
Suntharalingam et al., Conjugation of vitamin E analog α-TOS to Pt(IV) complexes for dual-targeting anticancer therapy. Chem Commun (Camb). Mar. 7, 2014;50(19):2465-8. doi: 10.1039/c3cc48740g. Epub Jan. 23, 2014.
Takahara et al., Crystal structure of the anticancer drug cisplatin bound to duplex DNA. J Am Chem Soc. 1996;118:12309-21.
Thoppil et al., Terpenoids as potential chemopreventive and therapeutic agents in liver cancer. World J Hepatol. Sep. 27, 2011;3(9):228-49. doi: 10.4254/wjh.v3.i9.228.
Todd et al., Inhibition of transcription by platinum antitumor compounds. Metallomics. 2009;1(4):280-91. doi: 10.1039/b907567d.
Trafton, MIT researchers see alternative to common colorectal cancer drug. News Office. Jun. 17, 2008. Last accessed Jun. 23, 2008. 2 pages.
Van Zutphen et al., Combinatorial discovery of new asymmetric cis platinum anticancer complexes is made possible with solid-phase synthetic methods. J Inorg Biochem. Oct. 2005;99(10):2032-8.
Van Zutphen et al., Extending solid-phase methods in inorganic synthesis: the first dinuclear platinum complex synthesised via the solid phase. Chem Commun (Camb). Mar. 7, 2003;(5):634-5.
Walker et al., Influence of the antioestrogen tamoxifen on normal breast tissue. Br J Cancer. Oct. 1991;64(4):764-8.
Wang et al., Cellular processing of platinum anticancer drugs. Nat Rev Drug Discov. Apr. 2005;4(4):307-20.
Wang et al., X-ray structure and mechanism of RNA polymerase II stalled at an antineoplastic monofunctional platinum-DNA adduct. Proc Natl Acad Sci U S A. May 25, 2010;107(21):9584-9. doi: 10.1073/pnas.1002565107. Epub May 6, 2010.
Weiss et al., New cisplatin analogues in development. A review. Drugs. Sep. 1993;46(3):360-77.
Whittaker et al., The interaction of DNA-targeted platinum phenanthridinium complexes with DNA. Nucleic Acids Res. Sep. 1, 1998;26(17):3933-9.
Wilson et al., Acetate-bridged platinum(III) complexes derived from cisplatin. Inorg Chem. Sep. 17, 2012;51(18):9852-64. doi: 10.1021/ic301289j. Epub Sep. 4, 2012.
Wilson et al., In vitro anticancer activity of cis-diammineplatinum(II) complexes with β-diketonate leaving group ligands. J Med Chem. Jun. 14, 2012;55(11):5326-36. doi: 10.1021/jm3002857. Epub May 18, 2012.
Wilson et al., Synthesis, characterization, and cytotoxicity of platinum(IV) carbamate complexes. Inorg Chem. Apr. 4, 2011;50(7):3103-15. doi: 10.1021/ic2000816. Epub Mar. 1, 2011.
Wilson, New Constructs for Platinum Anticancer Prodrugs. Presentation. Oct. 19, 2011. 41 pages.
Wisnovsky et al., Targeting mitochondrial DNA with a platinum-based anticancer agent. Chem Biol. Nov. 21, 2013;20(11):1323-8. doi: 10.1016/j.chembiol.2013.08.010. Epub Oct. 31, 2013.
Wong et al., Current status of platinum-based antitumor drugs. Chem Rev. Sep. 8, 1999;99(9):2451-66.
Wong et al., Harnessing chemoselective imine ligation for tethering bioactive molecules to platinum(IV) prodrugs. Dalton Trans. May 28, 2012;41(20):6104-11. doi: 10.1039/c2dt30264k. Epub Mar. 16, 2012.
Yalçin, Studies on cis-DDP, [Pt(Dach)(MePhSO)Cl]+ and [PtNH3)2(N-Py)Cl]+ binding to fumarase. Drug Metabol Drug Interact. 1995;12(2):105-15.
Yonezawa et al., Cisplatin and oxaliplatin, but not carboplatin and nedaplatin, are substrates for human organic cation transporters (SLC22A1-3 and multidrug and toxin extrusion family). J Pharmacol Exp Ther. Nov. 2006;319(2):879-86. Epub Aug. 16, 2006.
Zamble et al., Cisplatin and DNA repair in cancer chemotherapy. Trends Biochem Sci. Oct. 1995;20(10):435-9.
Zamble et al., Repair of cisplatin-DNA adducts by the mammalian excision nuclease. Biochemistry. Aug. 6, 1996;35(31):10004-13.
Zhang et al., Organic cation transporters are determinants of oxaliplatin cytotoxicity. Cancer Res. Sep. 1, 2006;66(17):8847-57.
Zhu et al., Monofunctional platinum-DNA adducts are strong inhibitors of transcription and substrates for nucleotide excision repair in live mammalian cells. Cancer Res. Feb. 1, 2012;72(3):790-800. doi: 10.1158/0008-5472.CAN-11-3151. Epub Dec. 16, 2011.
Zorbas-Seifried et al., Reversion of structure-activity relationships of antitumor platinum complexes by acetoxime but not hydroxylamine ligands. Mol Pharmacol. Jan. 2007;71(1):357-65.
International Preliminary Report on Patentability for PCT/US2014/33011 mailed Oct. 15, 2015.
Kallio et al., Role of mitochondria in tamoxifen-induced rapid death of MCF-7 breast cancer cells. Apoptosis. Dec. 2005;10(6):1395-410.
Mi et al., Vitamin E TPGS prodrug micelles for hydrophilic drug delivery with neuroprotective effects. Int J Pharm. Nov. 15, 2012;438(1-2):98-106. doi: 10.1016/j.ijpharm.2012.08.038. Epub Aug. 29, 2012.
Toogood, Mitochondrial drugs. Curr Opin Chem Biol. Aug. 2008;12(4):457-63. Epub Jul. 2, 2008.
U.S. Appl. No. 13/060,354, filed May 16, 2011, Lippard et al.
U.S. Appl. No. 13/529,965, filed Jun. 21, 2012, Lippard et al.
U.S. Appl. No. 14/209,089, filed Mar. 13, 2014, Lippard et al.
PCT/US2014/33011, mailed Aug. 22, 2014, Invitation to Pay Additional Fees.
PCT/US2014/33011, mailed Oct. 31, 2014, International Search Report and Written Opinion.

* cited by examiner

Pt-MPP

Pt-MPP(TAMRA)

US 9,593,139 B2

COMPOSITIONS, METHODS, AND KITS COMPRISING PLATINUM COMPOUNDS ASSOCIATED WITH A LIGAND COMPRISING A TARGETING MOIETY

RELATED APPLICATIONS

This application claims priority under 35 U.S.C. §119(e) to U.S. Provisional Application Ser. No. 61/808,874, filed Apr. 5, 2013 which is incorporated herein by reference in its entirety.

FIELD

Compositions, kits, and methods for treatment of cancers are generally provided. In some embodiments, the compositions, kits, and methods comprise a platinum (e.g., Pt(II) or Pt(IV)) compound associated with a ligand (e.g., a beta-diketonate ligand) comprising a targeting moiety. Methods of synthesizing platinum (e.g., Pt(II) or Pt(IV)) compounds associated with a ligand comprising a targeting moiety are also provided.

STATEMENT REGARDING FEDERALLY SPONSORED RESEARCH OR DEVELOPMENT

This invention was made with Government support under Grant No. R01 GM065519 awarded by the National Institutes of Health. The Government has certain rights in the invention.

BACKGROUND

Cisplatin (cis-diamminedichloroplatinum(II)]) is an effective anticancer drug that has been used in the clinic since it received FDA approval in 1978. The second-generation platinum-based anticancer drugs, carboplatin (cis-diammine (1,1'-cyclobutanedicarboxylatoplatinum(II))), and oxaliplatin ((R,R-1,2-diaminocyclohexane)oxalatoplatinum(II)), are also commonly used. These three compounds are considered to operate by similar mechanism of action; the cis-diam(m) ine platinum group binds to nuclear DNA, inducing apoptosis by transcription inhibition and its downstream effects. Challenges associated with currently approved platinum-based drugs include toxic side effects of these agents and the development of resistance towards them, both of which limit the broader utility and necessitate development of new platinum drug candidates.

Accordingly, improved compositions and methods are needed.

SUMMARY

In some embodiments, a compound is provided having the structure:

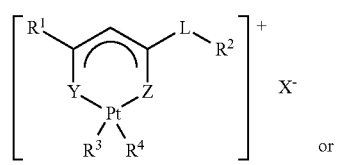

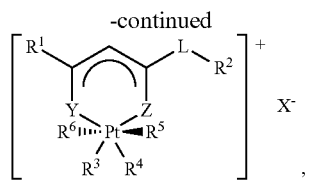

wherein:
$R^1$ is selected from the group consisting of alkyl optionally substituted, heteroalkyl optionally substituted, and aryl optionally substituted;
$R^2$ comprises a targeting moiety;
$R^3$ and $R^4$ are independently selected from the group consisting of ammonia, an optionally substituted heterocycle including at least one nitrogen, and an optionally substituted amine, or $R^3$ and $R^4$ can be joined together to form a bidentate ligand;
$R^5$ and $R^6$ are independently selected from the group consisting of hydroxyl, alkoxy, aryloxy, and acyloxy, each optionally substituted;
L is a linking group;
Z and Y are independently selected from the group consisting of O and S; and
$X^-$ is a counterion.

In some embodiments, a method is provided, comprising: reacting a precursor compound having the structure:

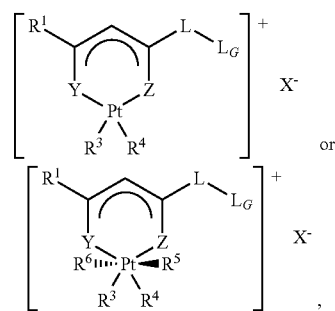

with a reactant comprising $R^2$ to form a compound having the structure:

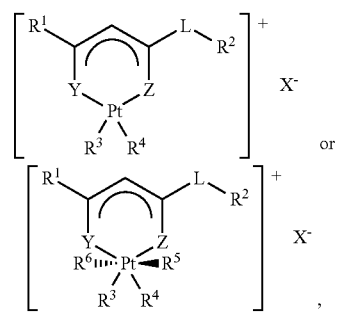

wherein:
$R^1$ is selected from the group consisting of alkyl optionally substituted, heteroalkyl optionally substituted, and aryl optionally substituted;
$R^2$ comprises a targeting moiety;
$R^3$ and $R^4$ are independently selected from the group consisting of ammonia, an optionally substituted heterocycle including at least one nitrogen, and an optionally substituted amine, or $R^3$ and $R^4$ can be joined together to form a bidentate ligand;

$R^5$ and $R^6$ are independently selected from the group consisting of hydroxyl, alkoxy, aryloxy, and acyloxy, each optionally substituted;

L is a linking group;

$L_G$ is a group capable of reacting with the reactant comprising $R^2$;

Z and Y are independently selected from the group consisting of O and S; and $X^-$ is a counterion.

Figure 1:
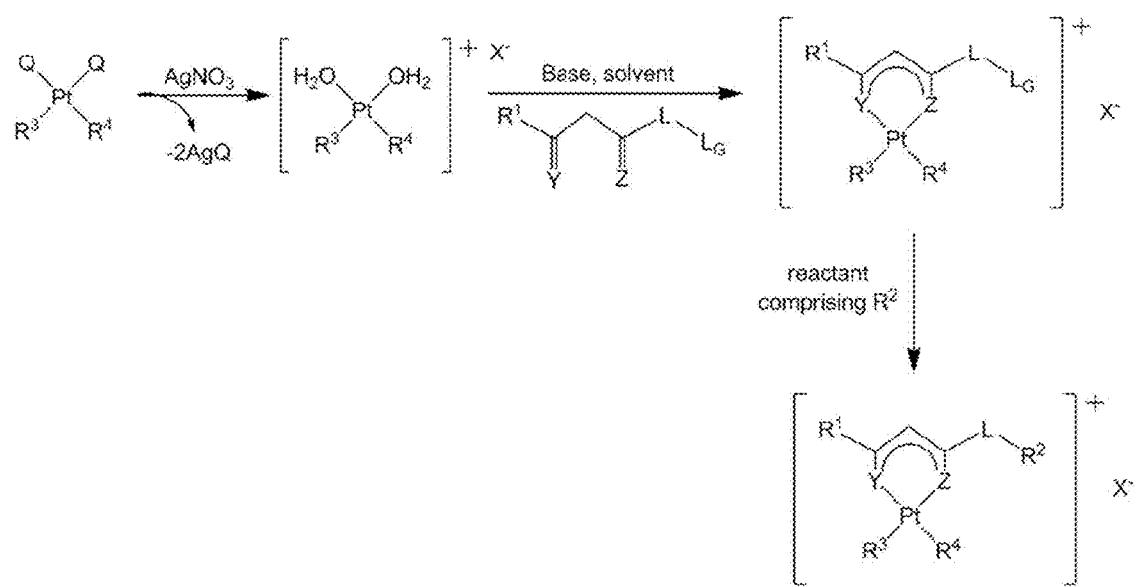
FIG. 1 shows a non-limiting example of a synthetic schematic for making diamineplatinum(II) β-diketonate compounds comprising a carboxylic acid moiety, following by association with a targeting moiety, according to some embodiments.

Other aspects, embodiments, and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

Compositions, kits, and methods useful for treating subjects having cancer or at risk of developing cancer are generally provided. In some embodiments, the compositions, kits, and methods comprise a platinum (e.g., Pt(II) or Pt(IV)) compound associated with a ligand (e.g., a beta-diketonate ligand) comprising a targeting moiety. Methods of synthesizing platinum (e.g., Pt(II) or Pt(IV)) compounds associated with a ligand (e.g., a beta-diketonate ligand) comprising a targeting moiety are also provided.

In some embodiments, compounds and related compositions for use in treating subjects known to have (e.g., diagnosed with) cancer or subjects at risk of developing cancer are provided. In some embodiments, methods described herein include administering to a subject a therapeutically effective amount of a compound, or a therapeutic preparation, composition, or formulation of the compound as described herein, to a subject having a cancer, who is otherwise free of indications for treatment with said compound. In a particular embodiment, the subject is a human.

In some embodiments, a compound is provided having the structure:

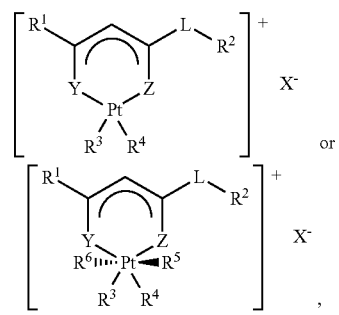

wherein:

$R^1$ is selected from the group consisting of alkyl optionally substituted, heteroalkyl optionally substituted, and aryl optionally substituted;

$R^2$ comprises a targeting moiety;

$R^3$ and $R^4$ are independently selected from the group consisting of ammonia, an optionally substituted heterocycle including at least one nitrogen, and an optionally substituted amine, or $R^3$ and $R^4$ can be joined together to form a bidentate ligand;

$R^5$ and $R^6$ are independently selected from the group consisting of hydroxyl, alkoxy, aryloxy, and acyloxy, each optionally substituted;

L is a linking group;

Z and Y are independently selected from the group consisting of O and S; and $X^-$ is a counterion. In some embodiments, $R^2$ is a targeting moiety.

In some embodiments, $R^1$ is substituted or unsubstituted alkyl. In some embodiments, $R^1$ is methyl. In some embodiments, $R^1$ is haloalkyl, for example, $CF_3$. In some embodiments, $R^1$ is substituted or unsubstituted cycloalkyl (e.g., cyclohexyl). In some embodiments, $R^1$ is substituted or unsubstituted heterocylcoalkyl (e.g., adamantyl). In some embodiments, $R^1$ is substituted or unsubstituted aryl. In some embodiments, $R^1$ is substituted or unsubstituted phenyl. In some embodiments, $R^1$ is unsubstituted phenyl. In some embodiments, $R^1$ is cycloalkyl.

In some embodiments, $R^2$ comprises a targeting moiety. In some embodiments, $R^2$ is a targeting moiety. The term "targeting moiety" is art-recognized and is used herein to refer to a moiety that localizes to or away from a specific locale (e.g., in a subject). For example, in some embodiments, the targeting agent aids in directing the platinum compound to a specific tissue or location in a subject's body. Said locale may be a tissue, a particular cell type, or a subcellular compartment. In some embodiments, said locale or tissue/location in a subject may be a cancer.

Those of ordinary skill in the art will be aware of suitable targeting moieties, for example, a protein, a peptide, a nucleic acid, a nucleic acid analog, a carbohydrate, a small molecule, an antibody, and a nanoparticle (e.g., polymeric nanoparticle, gold nanoparticle, etc.). Other non-limiting examples of targeting moieties include sugars and polymers. In some embodiments, the targeting moiety is a moiety which targets a cancer. In some embodiments, the targeting moiety is a peptide. In some embodiments, the targeting moiety is a cell-penetrating peptide (CPP), for example, a mitochondria-penetrating peptide (MPP). A non-limiting example of an MPP is $(F_x r)_b$, wherein $F_x$ and r are cyclohexylalanine and d-arginine, respectively, and b is an integer greater than 1 (e.g., 2, 3, 4, 5, 6, 7, 8, 9, 10, etc.). In some embodiments, b is 2 to 20, or 2 to 10, or 2 to 5. In some embodiments, b is 3-5, or 2, or 3, or 4, or 5, or 6, or 7, or 8, or 9, or 10. Other non-limiting examples of cell-penetrating peptides include Tat peptide, oligoarginine (r9), oligolysine (k9), and penetratin. In some embodiments, the targeting moiety may be labelled (e.g., with a fluorescent moiety such as TAMRA) to aid in detection of the molecule. In some cases, the targeting moiety comprises a terminating group (e.g., a group associated with the terminal end of the targeting moiety which is not associated to the platinum compound via the linker). For example, in the case of where the targeting moiety comprises the MMP being $(F_xr)_b$, the targeting moiety may comprises the structure $(F_xr)_b$-(C=O)NH$_2$.

In some embodiments, $R^3$ and $R^4$ are independently selected from the group consisting of ammonia, an optionally substituted heterocycle comprising at least one nitrogen, and an optionally substituted amine. In some embodiments, at least one of or each of $R^3$ and $R^4$ is an optionally substituted amine comprising the structure $N(R^7)_3$, wherein each $R^7$ is independently selected from the group consisting of H, alkyl optionally substituted, and aryl optionally substituted, or optionally two $R^7$ are joined together to form a ring. Non-limiting example of amine groups include $NH_2Cy$ wherein Cy is cyclohexyl and $NH_2(CH_2Ph)$. In any of the above structures, in some embodiments, at least one of $R^3$ and $R^4$ is $NH_3$. In some embodiments, each of $R^3$ and $R^4$ is $NH_3$.

In some embodiments, $R^3$ and $R^4$ are joined together to form a ring so that $R^3$ and $R^4$ form a bidentate ligand. In some embodiments, each of $R^3$ and $R^4$ of the bidentate ligand is associated with the platinum metal center via a nitrogen-atom. A non-limiting example of bidentate ligand is —$N(R^7)_2(C(R^7)_2)_nC(R^7)$— wherein n is 2, 3, 4, 5, or 6 and $R^7$ is as described herein. Another non-limiting example of bidentate ligand is —$N(R^7)_2(C(R^7)_2)_nN(R^7)$— wherein n is 2, 3, 4, 5, or 6 and $R^7$ is as described herein. In some embodiments, each $R^7$ is independently selected from the group consisting of H, alkyl optionally substituted, and aryl optionally substituted, or optionally two $R^7$ are joined together to form a ring. In some cases, the bidentate ligand is —$NH_2(CH_2)_nNH_2$— wherein n is 2, 3, 4, 5, or 6. In some embodiments, $R^3$ and $R^4$ form the bidentate ligand:

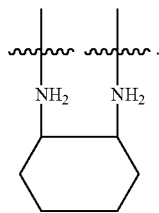 [SMILES: *NC1CCCCC1N*]

In some embodiments, at least one of or each of $R^3$ and $R^4$ may be an optionally substituted heterocycle groups including at least one nitrogen. In some embodiments, the at least one nitrogen is coordinated to the platinum. Non-limiting examples of heterocycle groups including at least one nitrogen include pyridine, imidazole, pyrazine, pyrimidine, pyridazine, acridine, acridin-9-amine, bipyridine, naphthyridine, quinoline, benzoquinoline, benzoisoquinoline, phenanthridine, phenanthridine-1,9-diamine, benzylamine, or substituted derivatives thereof.

In some embodiments, $R^5$ and $R^6$ are independently selected from the group consisting of hydroxyl, alkoxy, aryloxy, and acyloxy, each optionally substituted. Non-limiting examples of suitable $R^5$ and $R^6$ groups include —OH, —OAr (e.g., Ar=phenyl), —Obenzyl, and —OC(=O)$R^8$ wherein $R^8$ is hydrogen, optionally substituted alkyl, or optionally substituted aryl.

In some embodiments, each of Y and Z are oxygen, wherein the ligand is a beta-diketonate ligand. In some embodiments, Y is oxygen and Z is sulfur. In some embodiments Y is sulfur and Z is oxygen. In some embodiments, each of Y and Z are sulfur.

The linking group, L, may be any suitable linking group. In some embodiments, the linking group L is optionally substituted alkylene, optionally substituted arylene, optionally substituted heteroarylene, optionally substituted heteroalkylene, optionally substituted cycloalkylene, optionally substituted cycloheteroalkylene, —C(=O)—, —C(=O)O—, —NR$^7$—, —S—, —O—, or a combination thereof, wherein each $R^7$ is independently hydrogen or optionally substituted alkyl. In some embodiments, L comprises the structure —(CH$_2$)$_q$(C=O)— or —(CH$_2$)$_q$(C=O)NH— wherein q is an integer (e.g., q is 1-100, or q is between 1 and 100, or q is 1-50, or q is between 1 and 50, or q is 1-20, or q is between 1 and 20, or q is 1-10, or q is between 1 and 10, or 1, 2, 3, 4, 5, 6, 7, 8, 9, or 10). In some embodiments, L comprises the structure —[(CH$_2$)$_m$O]$_q$(C=O)— or —[(CH$_2$)$_m$O]$_q$(C=O)NH—, wherein q is an integer (e.g., q is 1-100, or q is between 1 and 100, or q is 1-50, or q is between 1 and 50, or q is 1-20, or q is between 1 and 20, or q is 1-10, or q is between 1 and 10, or 1, 2, 3, 4, 5, 6, 7, 8, 9, or 10) and each m is independently 1-6, or an integer between 1 and 6 (e.g., 1, 2, 3, 4, 5, or 6).

In some embodiments, a compound described herein may be a salt comprising a positively charged platinum metal center (e.g., associated with ligands) and a counterion (e.g., "X"). The counterion X may be a weak or non-nucleophilic stabilizing ion. X may have a charge of (−1), (−2), (−3), etc. In some cases, X has a charge of (−1). In other cases, X has a charge of (−2). Those of ordinary skill in the art will be aware of suitable stoichiometries for use with the compounds described herein. For example, in embodiments where the platinum has a charge of (+1) and the counterion has a charge of (−1), the ratio of the platinum to the counterion is generally 1:1. As another example, in embodiments where the platinum (e.g., associated with ligands) has a charge of (+1) and the counterion has a charge of (−2), the ratio of the platinum to the counterion is generally 1:2. In some cases, the counterion is a negatively charged and/or non-coordinating ion. In any of the above compounds, X may be any suitable counterion, including, but not limited to, halide (e.g., chloride, bromide, iodide), nitrate, nitrite, sulfate, sulfite, and triflate. In some embodiments, $X^1$ is halide, sulphate, or nitrate.

In some embodiments, $R^1$ and $R^2$ are each alkyl, $R^3$ and $R^4$ are each ammonia, -L-$R^2$ is (CH$_2$)$_t$(C=O)NH—$R^2$, and t is 1-20. In some embodiments, t is 1-10, or 1-5, or 1, 2, 3, 4, or 5. In some embodiments, $R^2$ comprises the structure $(F_xr)_b$C(=O)NH, wherein $F_R$ is cyclohexylalanine, r is d-arginine, respectively, and b is 2-20, or 2-10, or 2-5, or 3-5, or 2, or 3, or 4, or 5, or 6, or 7, or 8, or 9, or 10.

In some embodiments, the compound has the structure:

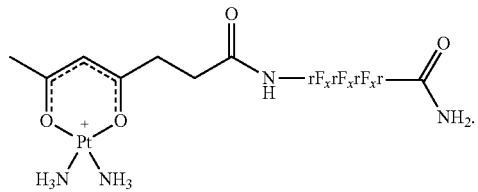

In some embodiments, methods are provided for synthesizing a compound having the structure:

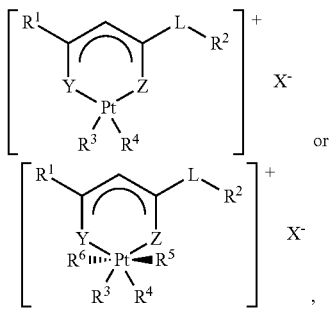

wherein each of $R^1$-$R^6$, X, Y, Z, and L are as described above. In some embodiments, the method comprises reacting a precursor compound having the structure:

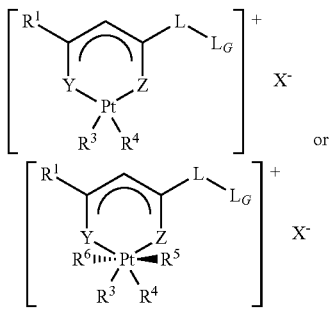

with a reactant comprising $R^2$ to form the compound, wherein $L_G$ is a group capable of reacting with the reactant comprising $R^2$ and each of $R^1$-$R^6$, X, Y, Z, and L are as described above with respect to the compounds. As will be understood by those of ordinary skill in the art, the compound formed may comprise some portion of the $L_G$ group and/or some portion of the reactant comprising $R^2$ other than the $R^2$ group. For example, in some embodiments, $L_G$ is —COOH and the reactant is $NH_2R^2$, wherein the reaction between the two moieties results in the group —C(=O)NHR$^2$ being present in the compound formed.

Those of ordinary skill in the art will be aware of suitable $L_G$ and reactants comprising $R^2$ for use with the methods described herein, wherein $L_G$ and the reactant comprising $R^2$ are reactive with each other, thereby associating the $R^2$ group with the compounds (e.g., via a covalent bond). Non-limiting examples of chemistries include reaction between a carboxylic acid (e.g., COOH) moiety and an amine moiety, click chemistry (e.g., reaction between an azide and an alkyne, or a reaction between tetrazine and cis-cyclooctene (e.g., see JACS 2008, 130, 13518)), ester coupling (e.g., reaction between a —COOH functional group and a —CH$_2$OH functional group, carbamate coupling (e.g., reaction between a —NHR group and a —NCO group), oxime and hydrazone ligation reaction (e.g., reaction of an aldehyde (e.g., —RCHO) with either a hydroxylamine (e.g., —RNHOH) or hydrazide (e.g., —RNHNH$_2$)), and reactions comprising a thiol (e.g., thiol couplings, such as with iodoacetamide or maleimide coupling; thiol/ene chemistry).

In some embodiments, -L-$L_G$ is -L-C(=O)OH and the reactant comprising $R^2$ comprises the structure $H_2N$—$R^2$, wherein -L-$R^2$ of the resulting product comprises the structure L-C(=O)—NHR$^2$. In other embodiments, -L-$L_G$ is -L-NH$_2$ and the reactant comprising $R^2$ comprises the structure $R^2$—COOH, wherein -L-$R^2$ of the resulting product comprises the structure -L-NH—C(=O)—R$^2$. In a particular embodiment, the reaction comprising reacting a compound having the structure:

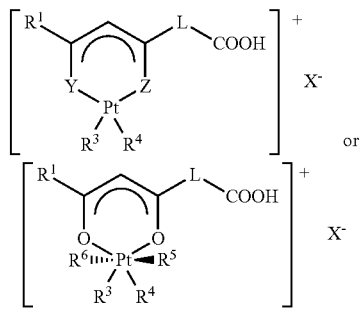

with a reactant comprising the structure NH$_2$R$^2$ to form a compound having the structure:

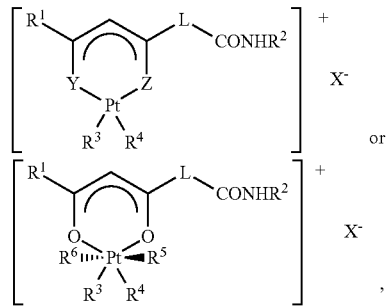

wherein $R^1$-$R^6$, Y, Z, L, and Z are as described herein. In some embodiments, each of Y and Z is oxygen. In some embodiments, L is alkylene. In some embodiments, L is heteroalkylene. In some embodiments, each of $R^3$ and $R^4$ are NH$_3$.

In some embodiments $L_G$ is a leaving group capable of reacting with the reactant comprising $R^2$. For example, the $R^2$ group may replace the leaving group or a portion of the leaving group. As used herein, the term "leaving group" is given its ordinary meaning in the art of synthetic organic chemistry and refers to an atom or a group capable of being displaced by a nucleophile. Examples of suitable leaving groups include, but are not limited to, halides (such as chloride, bromide, or iodide), alkoxycarbonyloxy, aryloxycarbonyloxy, alkanesulfonyloxy, arenesulfonyloxy, alkylcarbonyloxy (e.g., acetoxy), arylcarbonyloxy, aryloxy, methoxy, N,O-dimethylhydroxylamino, pixyl, haloformates, —NO$_2$, trialkylammonium, and aryliodonium salts. In some embodiments, the leaving group is a sulfonic acid ester. In some embodiments, the sulfonic acid ester comprises the formula —OSO$_2$R' wherein R' is selected from the group consisting alkyl optionally, alkenyl optionally substituted, heteroalkyl optionally substituted, aryl optionally substituted, heteroaryl optionally substituted, arylalkyl optionally substituted, and heterarylalkyl optionally substituted.

Those of ordinary skill in the art will be aware of suitable reaction conditions for carrying out the synthetic methods described herein. Conditions which may be varied include, but are not limited to, time of exposure, solvent, additives, temperature, and pressure. For example, in embodiments wherein a peptide (e.g., an MPP) is to be associated with a platinum compound via reaction or a carboxylic acid group, standard solid-phase methods may be employed (e.g., wherein the N-terminus of the peptide is associated with the platinum compound using a free carboxylic acid). For example, see S. I. Kirin, F. Noor, N. Metzler-Nolte and W. Mier, J. Chem. Educ., 2007, 84, 108-111. In some embodiments, the platinum compounds associated with the peptide may be cleaved from the solid support using an acid (e.g., trifluoroacetic acid) and optionally purified (e.g., via HPLC). In some embodiments, surprisingly, the use of trifluoroacetic acid may not sever any of the Pt-ligand bonds.

The synthetic methods described herein may be carried out in any suitable solvent, including, but are not limited to, non-halogenated hydrocarbon solvents (e.g., pentane, hexane, heptane, cyclohexane), halogenated hydrocarbon solvents (e.g., dichloromethane, chloroform, fluorobenzene, trifluoromethylbenzene), aromatic hydrocarbon solvents (e.g., toluene, benzene, xylene), ester solvents (e.g., ethyl acetate), ether solvents (e.g., tetrahydrofuran, dioxane, diethyl ether, dimethoxyethane), and alcohol solvents (e.g., ethanol, methanol, propanol, isopropanol, tert-butanol). Non-limiting examples of solvents useful include acetone, acetic acid, formic acid, dimethyl sulfoxide, dimethyl formamide, acetonitrile, p-cresol, glycol, petroleum ether, carbon tetrachloridetriethylamine, picoline, and pyridine.

A reaction may be carried out for any suitable period of time. In some cases, the reaction is carried out until the reaction is about 50%, about 60%, about 70%, about 80%, about 90%, about 93%, about 95%, about 96%, about 97%, about 98%, about 99%, about 99.5%, or greater, complete. That is, the reaction is carried out for a period of time until a selected percent of the starting material has been converted into a product. In some cases, the reaction is greater than about 50%, about 60%, about 70%, about 80%, about 90%, about 93%, about 95%, about 96%, about 97%, about 98%, about 99%, about 99.5%, or greater, complete in a period of time of less than about 24 hours, less than about 12 hours, less than about 8 hours, less than about 6 hours, less than about 5 hours, less than about 4 hours, less than about 3 hours, less than about 2 hours, less that about 1 hour, less than about 50 minutes, less than about 40 minutes, less than about 30 minutes, or less.

In some embodiments, the compound may comprise one or more organic or inorganic leaving groups. Additional ligands may coordinate to the metal center, including neutral ligands and/or charged ligands. Neutral ligands include ligands which may coordinate the metal center but do not alter the oxidation state of the metal center. For example, solvent molecules such as water, ammonia, pyridine, and acetonitrile may be neutral ligands. Charged ligands include ligands that may coordinate the metal center and may alter the oxidation state of the metal center. Examples of charged ligands include halides, carboxylates, and the like.

In some embodiments, the ligands associated with the platinum center in the platinum compound may include functional groups capable of interaction with a metal center, e.g., heteroatoms such as nitrogen, oxygen, sulfur, and phosphorus. Non-limiting examples of compounds which the ligands may comprise include amines (primary, secondary, and tertiary), aromatic amines, amino groups, amido groups, nitro groups, nitroso groups, amino alcohols, nitriles, imino groups, isonitriles, cyanates, isocyanates, phosphates, phosphonates, phosphites, (substituted) phosphines, phosphine oxides, phosphorothioates, phosphoramidates, phosphonamidites, hydroxyls, carbonyls (e.g., carboxyl, ester and formyl groups), aldehydes, ketones, ethers, carbamoyl groups, thiols, sulfides, thiocarbonyls (e.g., thiolcarboxyl, thiolester and thiolformyl groups), thioethers, mercaptans, sulfonic acids, sulfoxides, sulfates, sulfonates, sulfones, sulfonamides, sulfamoyls, and sulfinyls. In other cases, at least some of the ligands may be aryl group, alkenyl group, alkynyl group, or other moiety that may bind the metal atom in either a sigma- or pi-coordinated fashion.

In some embodiments, compounds described herein may comprise a bidentate ligand which, when bound to a metal center, forms a metallacycle structure with the metal center. Bidentate ligands suitable for use with the compounds described herein include species having at least two sites capable of binding to a metal center. For example, the bidentate ligand may comprise at least two heteroatoms that coordinate the metal center, or a heteroatom and an anionic carbon atom that coordinate the metal center. Examples of bidentate ligands suitable for use in the compounds described herein include, but are not limited to, alkyl and aryl derivatives of moieties such as amines, phosphines, phosphites, phosphates, thiolates, imines, oximes, ethers, hybrids thereof, substituted derivatives thereof, aryl groups (e.g., bis-aryl, heteroaryl-substituted aryl), heteroaryl groups, and the like. Specific examples of bidentate ligands include ethylene diamine, 2,2'-bipyridine, acetylacetonate, mono- and dithioacetylacetonate, oxalate, thiooxalate, and the like.

In some embodiments, compounds described herein may comprise a tridentate ligand, which includes species which have at least three sites capable of binding to a metal center. For example, the bidentate ligand may comprise at least three heteroatoms that coordinate the metal center, or a combination of heteroatom(s) and anionic carbon atom(s) that coordinate the metal center.

In some embodiments, the compounds comprise two leaving groups positioned in a cis configuration, i.e., the compound may be a cis isomer. However, it should be understood that compounds described herein may also have two leaving groups positioned in a trans configuration, i.e., the compound may be a trans isomer. Those of ordinary skill in the art would understand the meaning of these terms.

In some embodiments, a compound described herein has a molecular weight of 1500 g/mol or less, 1500 g/mol or less, 1400 g/mol or less, 1300 g/mol or less, 1200 g/mol or less, 1100 g/mol or less, 1000 g/mol or less, 900 g/mol or less, 800 g/mol or less, 700 g/mol or less (e.g., 700 Da or less).

Pt(II) and Pt(IV) compounds described herein may be synthesized according to methods known in the art, including various methods described herein. For example, the method may comprise reaction of cisplatin with one or more ligand sources, optionally followed by association of the targeting ligand (e.g., as described in more detail herein). For example, FIG. 1 illlustrates a non-limiting synthetic method, wherein $R^1$-$R^4$, L, $L_G$, X, Y, and Z are as described herein and Q is a leaving group. In some cases, Q is a halide (e.g., F, Cl, Br, or I). In some embodiments, the base is NaOH. In some embodiments, the solvent is water. In some embodiments, each of Y and Z are O. In some cases, a Pt(IV) compound can be obtained by reaction of the parent Pt(II) species with, for example, hydrogen peroxide at temperatures ranging between 25-60° C. in an appropriate solvent, such as water or N,N-dimethylformamide.

In some embodiments, a method for treating a subject having a cancer is provided comprising administering a therapeutically-effective amount of a compound as described herein to a subject having a cancer or suspective of having cancer. In some embodiments, a method is provided comprising promoting the inhibition or treatment of a cancer in a subject susceptible to or exhibiting symptoms of a cancer via administration to the patient of a composition comprising a compound as described herein. In some embodiments, a kit for treatment of a cancer is provided comprising a composition comprising a compound as described herein and instructions for use of the composition for treatment of a cancer. In some embodiments, a pharmaceutical composition is provided comprising a compound as described herein and one or more pharmaceutically acceptable carriers, additives, and/or diluents. In some embodiments, a composition for treating a subject having a cancer is provided wherein the composition comprises a compound as described herein. In some cases, the subject may be otherwise free of indications for treatment with said compound. In some cases, methods include use of cancer cells, including but not limited to mammalian cancer cells. In some instances, the mammalian cancer cells are human cancer cells.

In some embodiments, the compounds described herein have one or more desirable, but unexpected, combinations of properties, including increased activity and/or cytoxicity, and reduction of adverse side effects. In some embodiments, the compounds described herein are tunable and the substituents can be varied to provide the desirable balance between various properties, including lipophilicity and cell toxicity. For example, varying the targeting moiety can modulate the cytoxicity and/or resistance factors of the platinum compounds.

In some embodiments, a compound as described herein has a log P value (e.g., lipophilicity) of about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, or about 4.0, or greater, or any range of values there between. In some cases, a compound has a log P value of between about 0 and about 4, between about 1 and about 4, between about 2 and about 4, or between about 1 and about 3, or between about 1.5 and about 2.5, or between about 2 and about 3. In some cases, the log P value is about 2.15. Those of ordinary skill in the art will be aware of suitable methods for determining the log P value of a compound, for example, as described in the Examples section. In some embodiments, the log P value may be determined using the method described in the OECD Guidelines for the Testing of Chemicals, Test No. 107: Partition Coefficient (n-octanol/water): Shake Flask Method, adopted on Jul. 27, 1995. In some embodiments, the log P value may be tuned and/or selected by selection of the appropriate substituents on the beta-diketonate or related ligand.

In some embodiments, a compound as described herein has an $IC_{50}$ of about or less than about 30 uM (micromolar), about or less than about 28 uM, about or less than about 26 uM, about or less than about 24 uM, about or less than about 22 uM, about or less than about 20 uM, about or less than about 18 uM, about or less than about 16 uM, about or less than about 15 uM, about or less than about 14 uM, about or less than about 13 uM, about or less than about 12 uM, about or less than about 11 uM, about or less than about 10 uM, about or less than about 9 uM, about or less than about 8 uM, about or less than about 7 uM, about or less than about 6 uM, about or less than about 5 uM, about or less than about 4 uM, about or less than about 3 uM, about or less than about 2 uM, about or less than about 1.5 uM, about or less than about 1.0 uM, about or less than about 0.9 uM, about or less than about 0.8 uM, about or less than about 0.7 uM, about or less than about 0.6 uM, about or less than about 0.5 uM, about or less than about 0.4 uM, about or less than about 0.3 uM, about or less than about 0.2 uM, about or less than about 0.1 uM, or less.

In some embodiments, the compounds described herein substantially affect cancer cells and have no substantial effect on non-cancerous cells (e.g., the agent is substantially inactive towards non-cancerous cells) by determining the ratio of cancer cells which are affected (e.g., resulting in cell death by the agent) to non-cancerous cells which are affected, following exposure to the therapeutically active agent. For example, the ratio of cancer cells to non-cancerous cells which are affected (e.g., cell death) upon exposure to a therapeutically active agent is at least about 10:1, at least about 100:1, at least about 500:1, at least about 1000:1, at least about 5000:1, at least about 10,000:1, at least about 100,000:1, or greater. Those of ordinary skill in the art would be aware of methods and technologies for determining the ratio of cancerous cells to non-cancerous cells affected by the agent, as well as the number of cells that undergo cell death upon exposure to the agent. Other parameters may also be determined when determining whether an agent affects a cancer cell and/or a non-cancerous cell, for example, tumor size, membrane potential of a cell, or presence or absence of a compound in parts of the cell (e.g., cytochrome c, apoptosis inducing factor, etc.).

In some embodiments, the compounds described herein may be used to prevent the growth of a tumor or cancer, and/or to prevent the metastasis of a tumor or cancer. In some embodiments, compositions or compound described herein may be used to shrink or destroy a cancer. It should be appreciated that compositions or compound described herein may be used alone or in combination with one or more additional anti-cancer agents or treatments (e.g., chemotherapeutic agents, targeted therapeutic agents, pseudo-targeted therapeutic agents, hormones, radiation, surgery, etc., or any combination of two or more thereof). In some embodiments, a composition or compound described herein may be administered to a patient who has undergone a treatment involving surgery, radiation, and/or chemotherapy. In certain embodiments, a composition or compound described herein may be administered chronically to prevent, or reduce the risk of, a cancer recurrence.

The cancers treatable by methods described herein preferably occur in mammals. Mammals include, for example, humans and other primates, as well as pet or companion animals, such as dogs and cats, laboratory animals, such as rats, mice and rabbits, and farm animals, such as horses, pigs, sheep, and cattle. In some embodiments, the compounds described herein may be used to treat or affect cancers including, but not limited to lymphatic metastases, squamous cell carcinoma, particularly of the head and neck, esophageal squamous cell carcinoma, oral carcinoma, blood cell malignancies, including multiple myeloma, leukemias, including acute lymphocytic leukemia, acute nonlymphocytic leukemia, chronic lymphocytic leukemia, chronic myelocytic leukemia, and hairy cell leukemia, effusion lymphomas (body cavity based lymphomas), thymic lymphoma lung cancer, including small cell carcinoma, cutaneous T cell lymphoma, Hodgkin's lymphoma, non-Hodgkin's lymphoma, cancer of the adrenal cortex, ACTH-producing tumors, nonsmall cell cancers, breast cancer, including small cell carcinoma and ductal carcinoma, gastrointestinal cancers, including stomach cancer, colon cancer, colorectal cancer, polyps associated with colorectal neoplasia, pancreatic cancer, liver cancer, urological cancers, including bladder cancer, including primary superficial bladder tumors, invasive transitional cell carcinoma of the bladder, and muscle-invasive bladder cancer, prostate cancer, malignancies of the female genital tract, including ovarian carcinoma, primary peritoneal epithelial neoplasms, cervical carcinoma, uterine endometrial cancers, vaginal cancer, cancer of the vulva, uterine cancer and solid tumors in the ovarian follicle, malignancies of the male genital tract, including testicular cancer and penile cancer, kidney cancer, including renal cell carcinoma, brain cancer, including intrinsic brain tumors, neuroblastoma, astrocytic brain tumors, gliomas, metastatic tumor cell invasion in the central nervous system, bone cancers, including osteomas and osteosarcomas, skin cancers, including malignant melanoma, tumor progression of human skin keratinocytes, squamous cell cancer, thyroid cancer, retinoblastoma, neuroblastoma, peritoneal effusion, malignant pleural effusion, mesothelioma, gall bladder cancer, trophoblastic neoplasms, and hemangiopericytoma. In some cases, the cancer is lung, ovarian, cervix, breast, bone, colorectal, and/or prostate cancer. In some cases, the cancer is brain cancer or gliomas.

In some embodiments, the cancer is breast cancer. In some cases, the breast cancer is metastatic breast cancer. In some cases, the breast cancer is metastatic breast cancer that does not express the gene for the estrogen receptor (e.g., MDA-MB-468). In some cases, the breast cancer is triple-negative breast cancer that does not express the genes for the estrogen receptor, the progresterone receptor, or the Human Epidermal Growth Factor Receptor 2 (HER2).

In some embodiments, compositions (including pharmaceutical compositions), preparations, formulations, kits, and the like, comprising any of the compounds as described herein are provided. In some cases, a pharmaceutical composition is provided comprising a compound as described herein, or a pharmaceutically acceptable salt thereof, and one or more pharmaceutically acceptable carriers, additives and/or diluents. In some cases, a kit (e.g., for the treatment of cancer) comprises a composition (or a pharmaceutical composition) comprising a compound as described herein and instructions for use of the composition (or a pharmaceutical composition) for treatment of cancer. These and other embodiments of the invention may also involve promotion of the treatment of cancer or tumor according to any of the techniques and compositions and combinations of compositions described herein.

In some embodiments, "pharmaceutical compositions" or "pharmaceutically acceptable" compositions, which comprise a therapeutically effective amount of one or more of the compounds described herein, formulated together with one or more pharmaceutically acceptable carriers (additives) and/or diluents are provided. The pharmaceutical compositions described herein may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

As set out herein, certain embodiments of the compounds described herein may contain be formed or provided as a salt, and in some cases, as a pharmaceutically acceptable salt. The term "pharmaceutically-acceptable salt" in this respect refers to the relatively non-toxic, inorganic and organic salts of compounds described herein. These salts can be prepared in situ in the administration vehicle or the dosage form manufacturing process, or by separately reacting a purified compound described herein followed by reaction with a suitable reactant (e.g., suitable organic or inorganic acid and/or base), and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al., "Pharmaceutical Salts," J. Pharm. Sci. 1977, 66, 1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

The compound may be orally administered, parenterally administered, subcutaneously administered, and/or intravenously administered. In certain embodiments, a compound or pharmaceutical preparation is administered orally. In other embodiments, the compound or pharmaceutical preparation is administered intravenously. Alternative routes of administration include sublingual, intramuscular, and transdermal administrations.

Formulations include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient that can be combined with a carrier material to produce a single dosage form will vary depending upon the host being treated, and the particular mode of administration. The amount of active ingredient that can be combined with a carrier material to produce a single dosage form will generally be that amount of the compound which produces a therapeutic effect. Generally, this amount will range from about 1% to about 99% of active ingredient, from about 5% to about 70%, or from about 10% to about 30%.

In certain embodiments, a formulation comprises an excipient selected from the group consisting of cyclodextrins, liposomes, micelle forming agents, e.g., bile acids, and polymeric carriers, e.g., polyesters and polyanhydrides; and a compound described herein. In certain embodiments, an aforementioned formulation renders orally bioavailable a compound described herein.

Methods of preparing these formulations or compositions include the step of bringing into association a compound described herein with the carrier and, optionally, one or more accessory ingredients. In general, the formulations are prepared by uniformly and intimately bringing into association a compound described herein with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound described herein as an active ingredient. A compound described herein may also be administered as a bolus, electuary, or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and non-ionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent.

The tablets, and other solid dosage forms of the pharmaceutical compositions described herein, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds described herein include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions described herein for rectal or vaginal administration may be presented as a suppository, which may be prepared by mixing one or more compounds described herein with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations which are suitable for vaginal administration also include pessaries, tampons, creams, gels, pastes, foams or spray formulations containing such carriers as are known in the art to be appropriate.

Dosage forms for the topical or transdermal administration of a compound described herein include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams, and gels may contain, in addition to an active compound described herein, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound described herein, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound described herein to the body. Dissolving or dispersing the compound in the proper medium can make such dosage forms. Absorption enhancers can also be used to increase the flux of the compound across the skin. Either providing a rate controlling membrane or dispersing the compound in a polymer matrix or gel can control the rate of such flux.

Ophthalmic formulations, eye ointments, powders, solutions and the like, are also contemplated as being within the scope of this invention.

Pharmaceutical compositions described herein suitable for parenteral administration comprise one or more compounds described herein in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions described herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Delivery systems suitable for use with the present invention include time-release, delayed release, sustained release, or controlled release delivery systems, as described herein. Such systems may avoid repeated administrations of the active compounds of the invention in many cases, increasing convenience to the subject and the physician. Many types of release delivery systems are available and known to those of ordinary skill in the art. They include, for example, polymer based systems such as polylactic and/or polyglycolic acid, polyanhydrides, and polycaprolactone; nonpolymer systems that are lipid-based including sterols such as cholesterol, cholesterol esters, and fatty acids or neutral fats such as mono-, di- and triglycerides; hydrogel release systems; silastic systems; peptide based systems; wax coatings; compressed tablets using conventional binders and excipients; or partially fused implants. Specific examples include, but are not limited to, erosional systems in which the composition is contained in a form within a matrix, or diffusional systems in which an active component controls the release rate. The formulation may be as, for example, microspheres, hydrogels, polymeric reservoirs, cholesterol matrices, or polymeric systems. In some embodiments, the system may allow sustained or controlled release of the active compound to occur, for example, through control of the diffusion or erosion/degradation rate of the formulation. In addition, a pump-based hardware delivery system may be used in some embodiment of the invention.

Use of a long-term release implant may be particularly suitable in some cases. "Long-term release," as used herein, means that the implant is constructed and arranged to deliver therapeutic levels of the composition for at least about 30 or about 45 days, for at least about 60 or about 90 days, or even longer in some cases. Long-term release implants are well known to those of ordinary skill in the art, and include some of the release systems described above.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the compounds of the present invention are administered as pharmaceuticals, to humans and animals, they can be given per se or as a pharmaceutical composition containing, for example, about 0.1% to about 99.5%, about 0.5% to about 90%, or the like, of active ingredient in combination with a pharmaceutically acceptable carrier.

The administration may be localized (i.e., to a particular region, physiological system, tissue, organ, or cell type) or systemic, depending on the condition to be treated. For example, the composition may be administered through parental injection, implantation, orally, vaginally, rectally, buccally, pulmonary, topically, nasally, transdermally, surgical administration, or any other method of administration where access to the target by the composition is achieved. Examples of parental modalities that can be used with the invention include intravenous, intradermal, subcutaneous, intracavity, intramuscular, intraperitoneal, epidural, or intrathecal. Examples of implantation modalities include any implantable or injectable drug delivery system. Oral administration may be useful for some treatments because of the convenience to the patient as well as the dosing schedule.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

The compositions of the present invention may be given in dosages, generally, at the maximum amount while avoiding or minimizing any potentially detrimental side effects. The compositions can be administered in effective amounts, alone or in a cocktail with other compounds, for example, other compounds that can be used to treat cancer. An effective amount is generally an amount sufficient to inhibit cancer within the subject.

One of skill in the art can determine what an effective amount of the composition is by screening the ability of the composition using any of the assays described herein. The effective amounts will depend, of course, on factors such as the severity of the condition being treated; individual patient parameters including age, physical condition, size, and weight; concurrent treatments; the frequency of treatment; or the mode of administration. These factors are well known to those of ordinary skill in the art and can be addressed with no more than routine experimentation. In some cases, a maximum dose be used, that is, the highest safe dose according to sound medical judgment.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required to achieve the desired therapeutic effect and then gradually increasing the dosage until the desired effect is achieved.

In some embodiments, a compound or pharmaceutical composition of the invention is provided to a subject chronically. Chronic treatments include any form of repeated administration for an extended period of time, such as repeated administrations for one or more months, between a month and a year, one or more years, or longer. In many embodiments, a chronic treatment involves administering a compound or pharmaceutical composition of the invention repeatedly over the life of the subject. For example, chronic treatments may involve regular administrations, for example one or more times a day, one or more times a week, or one or more times a month. In general, a suitable dose such as a daily dose of a compound of the invention will be that amount of the compound that is the lowest dose effective to produce a therapeutic effect. Such an effective dose will generally depend upon the factors described above. Generally doses of the compounds of this invention for a patient, when used for the indicated effects, will range from about 0.0001 to about 100 mg per kg of body weight per day. The daily dosage may range from 0.001 to 50 mg of compound per kg of body weight, or from 0.01 to about 10 mg of compound per kg of body weight. In some cases, the dose may range from between about 5 and about 50 mg of compound per kg of body weight, between about 10 and about 40 mg of compound per kg of body weight, between about 10 and about 35 mg of compound per kg of body weight, or between about 15 and about 40 mg of compound per kg of body weight. However, lower or higher doses can be used. In some embodiments, the dose administered to a subject may be modified as the physiology of the subject changes due to age, disease progression, weight, or other factors.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it may be administered as a pharmaceutical formulation (composition) as described above.

The present invention also provides any of the above-mentioned compositions useful for treatment of cancer packaged in kits, optionally including instructions for use of the composition for the treatment of cancer. That is, the kit can include a description of use of the composition for participation in any biological or chemical mechanism disclosed herein associated with cancer or tumor. The kits can further include a description of activity of cancer in treating the pathology, as opposed to the symptoms of the cancer. That is, the kit can include a description of use of the compositions as discussed herein. The kit also can include instructions for use of a combination of two or more compositions of the invention. Instructions also may be provided for administering the drug by any suitable technique, such as orally, intravenously, or via another known route of drug delivery. The invention also involves promotion of the treatment of cancer according to any of the techniques and compositions and composition combinations described herein.

The compositions of the invention, in some embodiments, may be promoted for treatment of abnormal cell proliferation, cancers, or tumors, or includes instructions for treatment of accompany cell proliferation, cancers, or tumors, as mentioned above. In another aspect, the invention provides a method involving promoting the prevention or treatment of cancer via administration of any one of the compositions of the present invention, and homologs, analogs, derivatives, enantiomers and functionally equivalent compositions thereof in which the composition is able to treat cancers. As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention in connection with treatment of cell proliferation, cancers or tumors. "Instructions" can define a component of promotion, and typically involve written instructions on or associated with packaging of compositions of the invention. Instructions also can include any oral or electronic instructions provided in any manner. The "kit" typically defines a package including any one or a combination of the compositions of the invention and the instructions, or homologs, analogs, derivatives, enantiomers and functionally equivalent compositions thereof, but can also include the composition of the invention and instructions of any form that are provided in connection with the composition in a manner such that a clinical professional will clearly recognize that the instructions are to be associated with the specific composition.

The kits described herein may also contain one or more containers, which can contain compounds such as the species, signaling entities, biomolecules, and/or particles as described. The kits also may contain instructions for mixing, diluting, and/or administrating the compounds. The kits also can include other containers with one or more solvents, surfactants, preservatives, and/or diluents (e.g., normal saline (0.9% NaCl), or 5% dextrose) as well as containers for mixing, diluting or administering the components to the sample or to the patient in need of such treatment.

The compositions of the kit may be provided as any suitable form, for example, as liquid solutions or as dried powders. When the composition provided is a dry powder, the powder may be reconstituted by the addition of a suitable solvent, which may also be provided. In embodiments where liquid forms of the composition are sued, the liquid form may be concentrated or ready to use. The solvent will depend on the compound and the mode of use or administration. Suitable solvents for drug compositions are well known and are available in the literature. The solvent will depend on the compound and the mode of use or administration.

The kit, in one set of embodiments, may comprise a carrier means being compartmentalized to receive in close confinement one or more container means such as vials, tubes, and the like, each of the container means comprising one of the separate elements to be used in the method. For example, one of the container means may comprise a positive control in the assay. Additionally, the kit may include containers for other components, for example, buffers useful in the assay.

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

As used herein, a "subject" or a "patient" refers to any mammal (e.g., a human), such as a mammal that may be susceptible to tumorigenesis or cancer. Examples include a human, a non-human primate, a cow, a horse, a pig, a sheep, a goat, a dog, a cat, or a rodent such as a mouse, a rat, a hamster, or a guinea pig. In some embodiments, the subject is a human. In some embodiments, the subject is non-human. A subject may be a subject diagnosed with cancer or otherwise known to have cancer. In certain embodiments, a subject may be selected for treatment on the basis of a known cancer in the subject. In some embodiments, a subject may be selected for treatment on the basis of a suspected cancer in the subject. In some embodiments, a cancer may be diagnosed by detecting a mutation associate in a biological sample (e.g., urine, sputum, whole blood, serum, stool, etc., or any combination thereof. Accordingly, a compound or composition of the invention may be administered to a subject based, at least in part, on the fact that a mutation is detected in at least one sample (e.g., biopsy sample or any other biological sample) obtained from the subject. In some embodiments, a cancer may not have been detected or located in the subject, but the presence of a mutation associated with a cancer in at least one biological sample may be sufficient to prescribe or administer one or more compositions of the invention to the subject. In some embodiments, the composition may be administered to prevent the development of a cancer. However, in some embodiments, the presence of an existing cancer may be suspected, but not yet identified, and a composition of the invention may be administered to prevent further growth or development of the cancer.

It should be appreciated that any suitable technique may be used to identify or detect mutation and/or over-expression associated with a cancer. For example, nucleic acid detection techniques (e.g., sequencing, hybridization, etc.) or peptide detection techniques (e.g., sequencing, antibody-based detection, etc.) may be used. In some embodiments, other techniques may be used to detect or infer the presence of a cancer (e.g., histology, etc.).

The presence of a cancer can be detected or inferred by detecting a mutation, over-expression, amplification, or any combination thereof at one or more other loci associated with a signaling pathway of a cancer.

A "sample," as used herein, is any cell, body tissue, or body fluid sample obtained from a subject. Non-limiting examples of body fluids include, for example, lymph, saliva, blood, urine, and the like. Samples of tissue and/or cells for use in the various methods described herein can be obtained through standard methods including, but not limited to, tissue biopsy, including punch biopsy and cell scraping, needle biopsy; or collection of blood or other bodily fluids by aspiration or other suitable methods.

The phrase "therapeutically effective amount" as used herein means that amount of a compound, material, or composition comprising a compound of the present invention which is effective for producing some desired therapeutic effect in a subject at a reasonable benefit/risk ratio applicable to any medical treatment. Accordingly, a therapeutically effective amount prevents, minimizes, or reverses disease progression associated with a cancer. Disease progression can be monitored by clinical observations, laboratory and imaging investigations apparent to a person skilled in the art. A therapeutically effective amount can be an amount that is effective in a single dose or an amount that is effective as part of a multi-dose therapy, for example an amount that is administered in two or more doses or an amount that is administered chronically.

Definitions of specific functional groups and chemical terms are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito: 1999, the entire contents of which are incorporated herein by reference.

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

As used herein, the term "alkyl" is given its ordinary meaning in the art and refers to the radical of saturated aliphatic groups, including straight-chain alkyl groups, branched-chain alkyl groups, cycloalkyl(alicyclic) groups, alkyl substituted cycloalkyl groups, and cycloalkyl substituted alkyl groups. In some cases, the alkyl group may be a lower alkyl group, i.e., an alkyl group having 1 to 10 carbon atoms (e.g., methyl, ethyl, propyl, butyl, pentyl, hexyl, heptyl, octyl, nonyl, or decyl). In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., $C_1$-$C_{12}$ for straight chain, $C_3$-$C_{12}$ for branched chain), 6 or fewer, or 4 or fewer. Likewise, cycloalkyls may have from 3-10 carbon atoms in their ring structure, or 5, 6 or 7 carbons in the ring structure. Examples of alkyl groups include, but are not limited to, methyl, ethyl, propyl, isopropyl, cyclopropyl, butyl, isobutyl, t-butyl, cyclobutyl, hexyl, and cyclohexyl.

The term "alkylene" as used herein refers to a bivalent alkyl group. An "alkylene" group is a polymethylene group, i.e., —$(CH_2)_z$—, wherein z is a positive integer, e.g., from 1 to 20, from 1 to 10, from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described herein for a substituted aliphatic group.

Generally, the suffix "-ene" is used to describe a bivalent group. Thus, any of the terms defined herein can be modified with the suffix "-ene" to describe a bivalent version of that moiety. For example, a bivalent carbocycle is "carbocyclylene", a bivalent aryl ring is "arylene", a bivalent benzene ring is "phenylene", a bivalent heterocycle is "heterocyclylene", a bivalent heteroaryl ring is "heteroarylene", a bivalent alkyl chain is "alkylene", a bivalent alkenyl chain is "alkenylene", a bivalent alkynyl chain is "alkynylene", a bivalent heteroalkyl chain is "heteroalkylene", a bivalent heteroalkenyl chain is "heteroalkenylene", a bivalent heteroalkynyl chain is "heteroalkynylene", and so forth.

The terms "alkenyl" and "alkynyl" are given their ordinary meaning in the art and refer to unsaturated aliphatic groups analogous in length and possible substitution to the alkyls described above, but that contain at least one double or triple bond respectively.

In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, allyl, n-butyl, sec-butyl, isobutyl, t-butyl, n-pentyl, sec-pentyl, isopentyl, t-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl(propargyl), 1-propynyl and the like.

The term "cycloalkyl," as used herein, refers specifically to groups having three to ten, preferably three to seven carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic, or heterocyclic moieties, may optionally be substituted with substituents including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$;

—CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "heteroaliphatic," as used herein, refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl", "heteroalkynyl", and the like. Furthermore, as used herein, the terms "heteroalkyl", "heteroalkenyl", "heteroalkynyl", and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-20 carbon atoms. Heteroaliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroalkyl" is given its ordinary meaning in the art and refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, alkoxyalkyl, amino, thioester, poly(ethylene glycol), and alkyl-substituted amino.

The terms "heteroalkenyl" and "heteroalkynyl" are given their ordinary meaning in the art and refer to unsaturated aliphatic groups analogous in length and possible substitution to the heteroalkyls described above, but that contain at least one double or triple bond respectively.

Some examples of substituents of the above-described aliphatic (and other) moieties of compounds of the invention include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CHF$_2$; —CH$_2$F; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alycyclic, heteroaliphatic, heterocyclic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "aryl" is given its ordinary meaning in the art and refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls and/or heterocyclyls. The aryl group may be optionally substituted, as described herein. Substituents include, but are not limited to, any of the previously mentioned substitutents, i.e., the substituents recited for aliphatic moieties, or for other moieties as disclosed herein, resulting in the formation of a stable compound. In some cases, an aryl group is a stable mono- or polycyclic unsaturated moiety having preferably 3-14 carbon atoms, each of which may be substituted or unsubstituted. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups.

The terms "heteroaryl" is given its ordinary meaning in the art and refers to aryl groups comprising at least one heteroatom as a ring atom. A "heteroaryl" is a stable heterocyclic or polyheterocyclic unsaturated moiety having preferably 3-14 carbon atoms, each of which may be substituted or unsubstituted. Substituents include, but are not limited to, any of the previously mentioned substitutents, i.e., the substituents recited for aliphatic moieties, or for other moieties as disclosed herein, resulting in the formation of a stable compound. In some cases, a heteroaryl is a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will also be appreciated that aryl and heteroaryl moieties, as defined herein may be attached via an alkyl or heteroalkyl moiety and thus also include -(alkyl)aryl, -(heteroalkyl)aryl, -(heteroalkyl)heteroaryl, and -(heteroalkyl) heteroaryl moieties. Thus, as used herein, the phrases "aryl or heteroaryl moieties" and "aryl, heteroaryl, -(alkyl)aryl, -(heteroalkyl)aryl, -(heteroalkyl)heteroaryl, and -(heteroalkyl)heteroaryl" are interchangeable. Substituents include, but are not limited to, any of the previously mentioned substituents, i.e., the substituents recited for aliphatic moieties, or for other moieties as disclosed herein, resulting in the formation of a stable compound.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CHF; —CHF; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)R$_x$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments described herein.

The term "heterocycle" is given its ordinary meaning in the art and refers to cyclic groups containing at least one heteroatom as a ring atom, in some cases, 1 to 3 heteroatoms as ring atoms, with the remainder of the ring atoms being carbon atoms. Suitable heteroatoms include oxygen, sulfur, nitrogen, phosphorus, and the like. In some cases, the heterocycle may be 3- to 10-membered ring structures or 3- to 7-membered rings, whose ring structures include one to four heteroatoms.

The term "heterocycle" may include heteroaryl groups, saturated heterocycles (e.g., cycloheteroalkyl) groups, or combinations thereof. The heterocycle may be a saturated molecule, or may comprise one or more double bonds. In some cases, the heterocycle is a nitrogen heterocycle, wherein at least one ring comprises at least one nitrogen ring atom. The heterocycles may be fused to other rings to form a polycylic heterocycle. The heterocycle may also be fused to a spirocyclic group. In some cases, the heterocycle may be attached to a compound via a nitrogen or a carbon atom in the ring.

Heterocycles include, for example, thiophene, benzothiophene, thianthrene, furan, tetrahydrofuran, pyran, isobenzofuran, chromene, xanthene, phenoxathiin, pyrrole, dihydropyrrole, pyrrolidine, imidazole, pyrazole, pyrazine, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, triazole, tetrazole, oxazole, isoxazole, thiazole, isothiazole, phenanthridine, acridine, pyrimidine, phenanthroline, phenazine, phenarsazine, phenothiazine, furazan, phenoxazine, pyrrolidine, oxolane, thiolane, oxazole, oxazine, piperidine, homopiperidine (hexamethyleneimine), piperazine (e.g., N-methyl piperazine), morpholine, lactones, lactams such as azetidinones and pyrrolidinones, sultams, sultones, other saturated and/or unsaturated derivatives thereof, and the like. The heterocyclic ring can be optionally substituted at one or more positions with such substituents as described herein. In some cases, the heterocycle may be bonded to a compound via a heteroatom ring atom (e.g., nitrogen). In some cases, the heterocycle may be bonded to a compound via a carbon ring atom. In some cases, the heterocycle is pyridine, imidazole, pyrazine, pyrimidine, pyridazine, acridine, acridin-9-amine, bipyridine, naphthyridine, quinoline, benzoquinoline, benzoisoquinoline, phenanthridine-1,9-diamine, or the like.

The terms "halo" and "halogen" as used herein refer to an atom selected from the group consisting of fluorine, chlorine, bromine, and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "amino," as used herein, refers to a primary (—NH$_2$), secondary (—NHR$_x$), tertiary (—NR$_x$R$_y$), or quaternary (—N$^+$R$_x$R$_y$R$_z$)amine, where R$_x$, R$_y$, and R$_z$ are independently an aliphatic, alicyclic, heteroaliphatic, heterocyclic, aryl, or heteroaryl moiety, as defined herein. Examples of amino groups include, but are not limited to, methylamino, dimethylamino, ethylamino, diethylamino, methylethylamino, iso-propylamino, piperidino, trimethylamino, and propylamino.

The term "alkyne" is given its ordinary meaning in the art and refers to branched or unbranched unsaturated hydrocarbon groups containing at least one triple bond. Non-limiting examples of alkynes include acetylene, propyne, 1-butyne, 2-butyne, and the like. The alkyne group may be substituted and/or have one or more hydrogen atoms replaced with a functional group, such as a hydroxyl, halogen, alkoxy, and/or aryl group.

The term "alkoxy" (or "alkyloxy"), or "thioalkyl" as used herein refers to an alkyl group, as previously defined, attached to the parent molecular moiety through an oxygen atom or through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkoxy, include but are not limited to, methoxy, ethoxy, propoxy, isopropoxy, n-butoxy, t-butoxy, neopentoxy and n-hexoxy. Examples of thioalkyl include, but are not limited to, methylthio, ethylthio, propylthio, isopropylthio, n-butylthio, and the like.

The term "aryloxy" refers to the group, —O-aryl.

The term "acyloxy" refers to the group, —O-acyl.

The term "alkoxyalkyl" refers to an alkyl group substituted with at least one alkoxy group (e.g., one, two, three, or more, alkoxy groups). For example, an alkoxyalkyl group may be —(C$_{1-6}$-alkyl)-O—(C$_{1-6}$-alkyl), optionally substituted. In some cases, the alkoxyalkyl group may be optionally substituted with another alkyoxyalkyl group (e.g., —(C$_{1-6}$-alkyl)-O—(C$_{1-6}$-alkyl)-O—(C$_{1-6}$-alkyl), optionally substituted.

It will be appreciated that the above groups and/or compounds, as described herein, may be optionally substituted with any number of substituents or functional moieties. That is, any of the above groups may be optionally substituted. As used herein, the term "substituted" is contemplated to include all permissible substituents of organic compounds, "permissible" being in the context of the chemical rules of valence known to those of ordinary skill in the art. In general, the term "substituted" whether preceeded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl group" must still comprise the phenyl moiety and cannot be modified by substitution, in this definition, to become, e.g., a pyridine ring. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful for the formation of an imaging agent or an imaging agent precursor. The term "stable," as used herein, preferably refers to compounds which possess stability sufficient to allow manufacture and which maintain the integrity of the compound for a sufficient period of time to be detected and preferably for a sufficient period of time to be useful for the purposes detailed herein.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, aryl, aryloxy, perhaloalkoxy, aralkoxy, heteroaryl, heteroaryloxy, heteroarylalkyl, heteroaralkoxy, azido, amino, halide, alkylthio, oxo, acylalkyl, carboxy esters, -carboxamido, acyloxy, aminoalkyl, alkylaminoaryl, alkylaryl, alkylaminoalkyl, alkoxyaryl, arylamino, aralkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl, and the like. In some embodiments, a substituent may also be an imaging moiety (e.g., $^{18}F$) or a group for associating an imaging moiety (e.g., a chelator).

Nitrogen-protecting groups are well known in the art and include those described in detail in Protecting Groups in Organic Synthesis, T. W. Greene and P. G. M. Wuts, $3^{rd}$ edition, John Wiley & Sons, 1999, incorporated herein by reference. For example, nitrogen protecting groups include, but are not limited to, carbamates (including methyl, ethyl and substituted ethyl carbamates (e.g., Troc), to name a few), amides, cyclic imide derivatives, N-alkyl and N-aryl amines, imine derivatives, and enamine derivatives, to name a few. In some embodiments, the nitrogen-protecting group is carbobenzyloxy (Cbz), p-methoxybenzyl carbonyl (MeOZ), t-butyloxycarbonyl (Boc), 9-fluorenylmethyloxycarbonyl (Fmoc), acetyl (Ac), benzoyl (Bz), benzyl (Bn), p-methoxybenzyl (PMB), 3,4-dimethoxybenzyl (DMPM), p-methoxyphenyl (PMP), or p-toluenesulfonyloxy (Ts).

These and other aspects of the present invention will be further appreciated upon consideration of the following Examples, which are intended to illustrate certain particular embodiments of the invention but are not intended to limit its scope, as defined by the claims.

EXAMPLES AND EMBODIMENTS

Example 1

The following example describes the synthesis and use of exemplary cationic platinum(II) complexes with β-diketonate leaving group ligands containing a carboxylic acid functional group for attaching peptides.

Small peptides can offer a viable avenue for targeting tumor cells. Certain peptide sequences can selectively target tumors, by binding to receptors that are over expressed in cancer cells, or specific organelles intracellularly, such as the mitochondria or nucleus. These properties have previously been exploited for selective drug delivery. The use of such peptides for the delivery of platinum-based anticancer agents may enhance their specificity and potency, potentially circumventing the problems of resistance and toxicity. Mitochondria-penetrating peptides (MPPs) are associated with platinum(II) β-diketonate complexes, which contain a non-coordinating carboxylic acid group. The platinum-peptide constructs were assembled by solid-phase peptide synthesis, thus demonstrating the broader utility of these complexes for use with a variety of different peptide sequences.

Two platinum(II) complexes, which contain β-diketonate ligands with a non-coordinating carboxylic acid moiety, were synthesized by the general method shown in FIG. 1. The synthetic methodology may be utilized to access a number of derivatives with different $R^3$ and $R^4$ ligands (e.g., amine ligands) and different bidentate (e.g., β-diketonate ligands) comprising a group reactive with a reactant comprising $R^2$. In some cases, -L-$L_G$ is —$(CH_2)_n$—COOH, wherein n is of varying length. Other possible groups are described herein.

Figure 2:
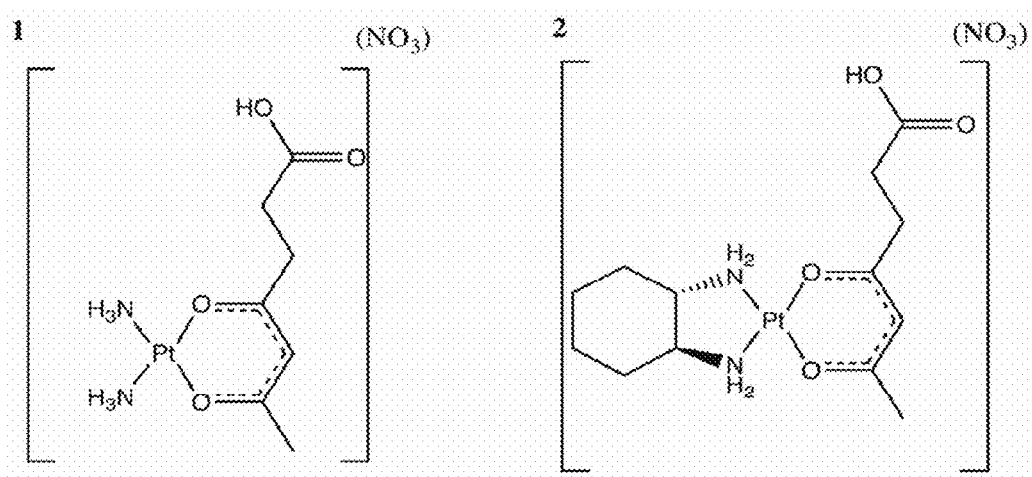
FIGS. 2 and 3 depict non-limiting examples of diamineplatinum(II) β-diketonate compounds, according to some embodiments.

The two complexes [Pt(am)(succac)]$NO_3$ (am=$(NH_3)_2$ or DACH=trans-1R,2R-diaminocyclohexane, succac=succinylacetonate) shown in FIG. 2 were synthesized by this method (e.g., FIG. 2). The complexes were characterized by multinuclear NMR spectroscopy, mass spectrometry, and X-ray crystallography. In FIG. 2: Pt(succac) complexes for N-terminus coupling to $(F_xr)_3$ MPP sequence.

The MPP, $F_xrF_xrF_xr$ (SEQ ID NO.: 1) where $F_x$ and r are the unnatural amino acids cyclohexylalanine and d-arginine, respectively, was synthesized by standard solid-phase methods. On the solid-phase, both [Pt(DACH)(succac)]$NO_3$ and [Pt(NH$_3$)$_2$(succac)]$NO_3$ were attached to the N-terminus of the peptide using the free carboxylic acid. The platinum-peptide conjugates were then cleaved from the resin with trifluoroacetic acid, purified by HPLC, and characterized by mass spectrometry. The use of trifluoroacetic acid did not sever any of the Pt-ligand bonds.

The cytotoxicities of the MPP-Pt conjugates were assessed in both the cisplatin-sensitive (A2780) and cisplatin-resistant (A2780/CP70) ovarian cancer cell lines. The corresponding 50% growth inhibitory concentrations ($IC_{50}$) are shown in Table 1 (see Example 2). The Pt-peptide conjugates ($[Pt(NH_3)_2(succac)-(F_xr)_3]$ and $[Pt(DACH)_2(succac)-(F_xr)_3]$) were less cytotoxic than the parent drugs cisplatin and oxaliplatin and were more cytotoxic than their peptide-free counterparts, $[Pt(NH_3)_2(succac)](NO_3)$ and $[Pt(DACH)(succac)](NO_3)$. The resistance factors (R.F.), defined as the ratio of the $IC_{50}$ values of the resistant and sensitive cell lines, were comparable for all of the complexes bearing the DACH non-leaving group ligand. For the diammineplatinum(II) complexes, the attachment of the MPP enabled the platinum to evade the resistance observed for the other two complexes (R.F.≈14 for cisplatin and $[Pt(NH_3)_2(succac)](NO_3)$. This result show that the use of a MPP can evade traditional cisplatin-resistance mechanisms.

The strategy presented here is useful for several reasons. For example, the Pt may be attached on the solid-phase as it inert to the harsh resin-cleavage conditions. The ability to use solid-phase chemistry to attach the Pt center simplifies purification and isolation of the desired compound. Additionally, the attachment point is the leaving group ligand, which does not directly affect the nature of the cytotoxic Pt-DNA adducts. Furthermore, these compounds utilize platinum in the +2 oxidation state, and hence the release of the peptide may be related to ligand substitution rather than the reduction kinetics, as may be the case for Pt(IV)-peptide conjugates.

From the above-mentioned cytoxicity data, it was demonstrated that the use of the proper peptide can modulate the cytoxicity and resistance factors for a given platinum compound. This methodology can be expanded to other peptide sequences to achieve the desired biological effects.

The diamineplatinum(II)β-diketonate complexes with non-coordinating carboxylic acid groups described in this example give access to a wide array of platinum anticancer agents tethered to peptides at the leaving group ligand. These constructs utilize both the high cytotoxicity of traditional platinum chemotherapeutics in combination with the organelle and tissue targeting properties of certain peptide sequences. As demonstrated with the case of platinated MPPs, $[Pt(DACH)(succac)(F_xr)_3]$ and $[Pt(NH_3)_2(succac)(F_xr)_3]$, peptide constructs coupled to diamineplatinum(II) β-diketonate complexes may overcome resistance. The use of other peptide sequences can potentially afford constructs that avoid toxic side effects normally associated with platinum-based chemotherapy.

Example 2

The following example provides additional details and experimental information relating to Example 1.

Because of its central role in mediating apoptosis, mitochondria are actively being explored as a potential anticancer drug targets. The mitochondria contain their own circular DNA (mtDNA). It is therefore of interest to consider the degree to which platinum-based drugs bind to mtDNA, and how these mtDNA lesions affect their overall mechanism of action. Previous studies have revealed that greater quantities of cispatin bind to mtDNA than to genomic DNA. The role of the mtDNA adducts is debated in the literature. On one hand, mitochondrial DNA damage by cisplatin in various tissues has been implicated as a mediator for the toxic side effects of the drug, including neuropathy, ototoxicity, and developmental toxicity. In contrast, other studies have proposed that the mitochondrial and not nuclear DNA is the critical target of cisplatin in potentiating its anticancer activity. The mitochondria also appear to play in role in mediating cellular resistance to cisplatin. Cisplatin-resistant cell lines have elevated mitochondrial membrane potentials, sustain less damage to mtDNA when treated with cisplatin, and exhibit substantially lower mitochondrial uptake of cisplatin compared to the non-resistant parent lines. Taken together, the abovementioned results point to an enigmatic role of the mitochondria in platinum-based chemotherapy.

To investigate the use of mitochonodria as a target for platinum-based chemotherapy, it would be advantageous to have a platinum complex that selectively localizes to this organelle. The use of cell-penetrating peptides (CPPs) to direct the platinum complex through the cell membrane into the desired organelle provides a viable strategy for preparing such a construct. In particular, mitochondria-penetrating peptides (MPPs), a subclass of CPPs, can be utilized. MPPs are typically short peptide sequences comprised of alternating lipophilic and cationic residues. The synthesis of a platinum(II) complex conjugated to the N-terminus of an MPP with the sequence $rF_xrF_xrF_xr$, where r is d-arginine and $F_x$ is l-cyclohexylalanine is provided. An additional construct with a carboxytetramethylrhodamine (TAMRA) dye was also prepared to facilitate cellular imaging studies. Cytotoxicity studies of the new mitochondria-targeted platinum complex reveal it to be equitoxic to both cisplatin-sensitive and -resistant ovarian cancer cell lines (A2780 and A2780CP70).

Experimental

General Materials and Methods

Small-molecule synthesis was carried out under normal atmospheric conditions with no precautions to exclude moisture or air. Cisplatin was purchased from Strem Chemicals and used as received. Succinylacetone was synthesized from ethyl acetate and levulinic acid as previously described.

Physical Measurements

NMR spectra were acquired on a Bruker DPX-400 spectrometer in the MIT Department of Chemistry Instrumentation Facility (DCIF). $^1H$ and $^{13}C$ NMR spectra were referenced to residual protons or the carbon nucleus of the deuterated methanol ($^1H$ δ=3.31 ppm, $^{13}C$ δ=49.1 ppm), and signals are reported versus TMS. For $^1H$ NMR spectra acquired in $D_2O$, signals were referenced to an internal standard of 1,4-dioxane (δ=3.75 ppm). $^{195}Pt$ NMR spectra were referenced externally to standard of $K_2PtCl_4$ in $D_2O$ (δ=−1628 ppm). For FTIR spectra, samples were prepared as KBr disks, and data was recorded with a ThermoNicolet Avatar 360 spectrophotometer running the OMNIC software. Electrospray ionization mass spectrometry (ESI-MS) measurements were acquired on an Agilent Technologies 1100 series LC-MSD trap. Solutions used for biological studies were dissolved in MilliQ water (or PBS for cisplatin) and sterile filtered. The platinum concentrations of the solutions were determined by graphite-furnace atomic absorption spectroscopy (GFAAS) using a Perkin-Elmer AAnalyst600 spectrometer. Elemental analyses were performed by a commercial analytical laboratory.

Synthesis of [Pt(succac)(NH$_3$)$_2$](NO$_3$)

Cisplatin (500 mg, 1.67 mmol) and AgNO$_3$ (552 mg, 3.25 mmol) were stirred together in 10 mL H$_2$O in the absence of light at room temperature for 16 h. The resulting mixture was filtered to remove AgCl. To the filtrate, a solution of NaOH (67 mg, 1.68 mmol) and succinylacetone (269 mg, 1.70 mmol) in 5 mL of H$_2$O was added dropwise. After stirring at rt for 5 h, the resulting solution was concentrated to dryness at 60° C. under reduced pressure to afford an orange oil. This oil was dissolved in 3 mL H$_2$O, acidified with three drops of 25% HNO$_3$. Acetone (50 mL) was added, and the resulting turbid white suspension was stirred for approximately 3 min, resulting in the deposition of an oily orange-brown residue. The turbid supernatant was decanted and mixed with 50 mL of a 1:1 (v/v) mixture of acetone and diethyl ether. Upon stirring at rt for approximately 5 min, an orange-brown residue deposited again. The cloudy supernatant was decanted and poured directly into 150 mL of diethyl ether. The mixture was stored at −40° C. for 1.5 h and filtered to collect a white solid. The white solid was washed with 2×10 mL diethyl ether and then dried in vacuo. Yield: 203 mg (28%). Mp 159-164° C. (dec). $^1$H NMR (400 MHz, MeOD-d$_4$): δ 5.65 (s, 1H), 4.44 (br s, 6H), 2.58 (t, 2H), 2.44 (t, 2H), 1.88 (s, 3H). $^{13}$C NMR (100 MHz, MeOD-d$_4$): δ 186.5, 186.3, 176.7, 102.7, 35.1, 31.0, 26.1. $^{195}$Pt NMR (86 MHz, MeOD-d$_4$): δ −1570. IR (KBr, cm$^{-1}$): 3432 m, 3285 s, 1708 m, 1563 s, 1524 s, 1384 vs, 1356 s, 1309 s, 1202 w, 1175 m, 1039 w, 807 w, 645 w. ESI-MS (+ mode, MeOH): m/z 386.1 (calcd. for [Pt(succac)(NH$_3$)$_2$]$^+$: 386.1). Anal. Calcd. for C$_7$H$_{15}$N$_3$O$_7$Pt: C, 18.75; H, 3.37; N, 9.37. Found: C, 19.04; H, 3.38; N, 9.27.

Synthesis of Pt-MPP, [Pt(succac)(NH$_3$)$_2$]-r(F$_x$r)$_3$-CONH$_2$ (also referred to in Example 1 as [Pt(NH$_3$)$_2$(succac-(F$_x$r)$_3$)])

Figure 3:
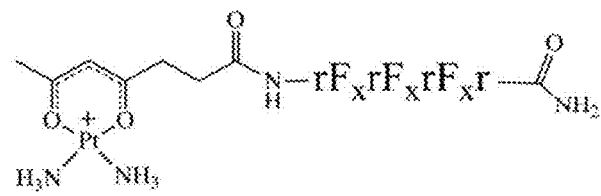
Figure 3:
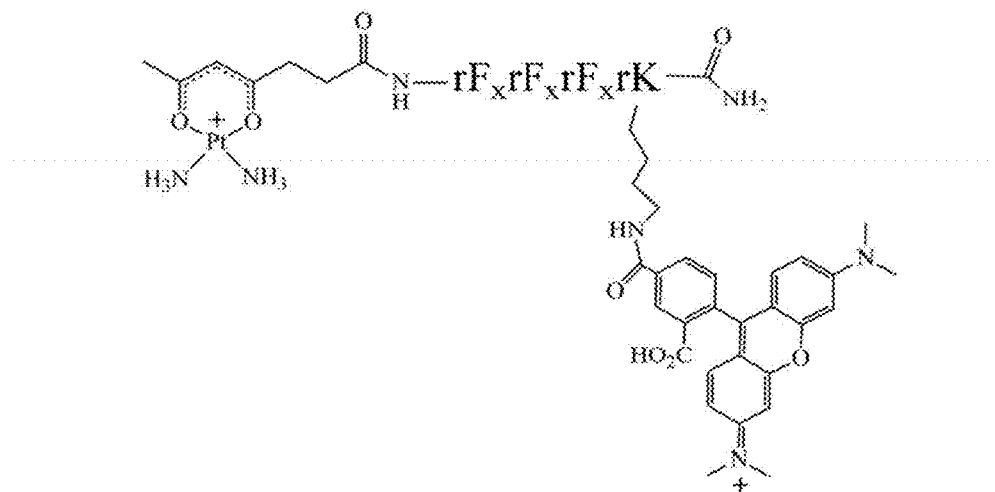
Figure 4A:
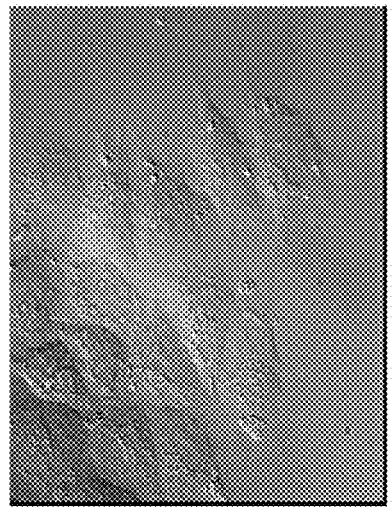
FIGS. 4A-H and 5A-H show images of cells treated with exemplary platinum compounds, according to some embodiments.
Figure 4B:
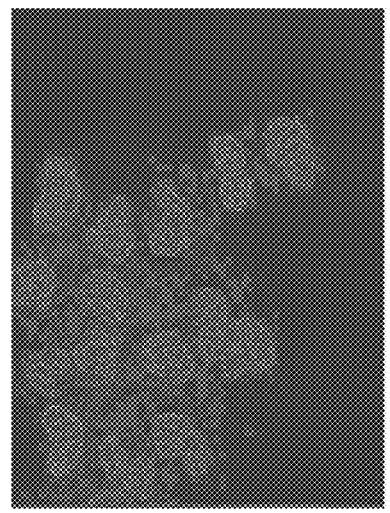
Figure 4C:
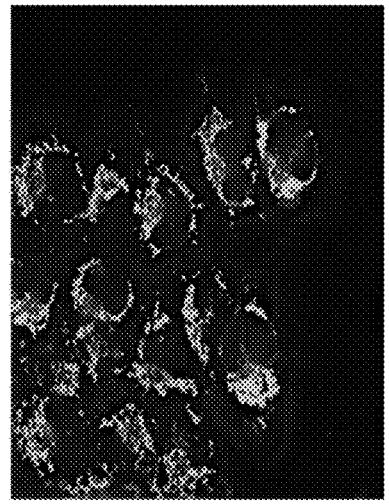
Figure 4D:
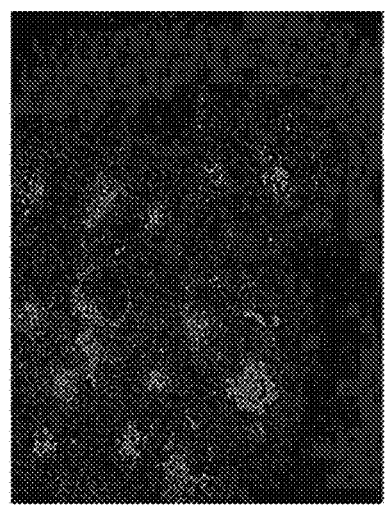
Figure 4E:
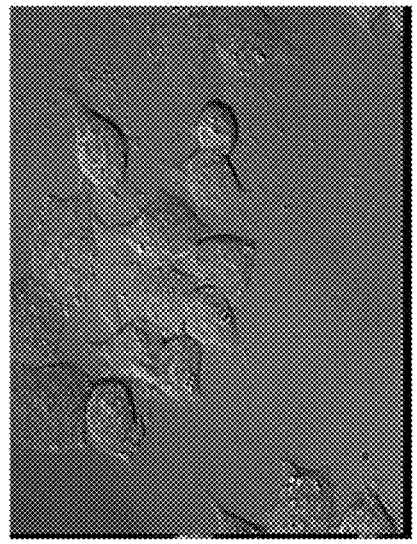
Figure 4F:
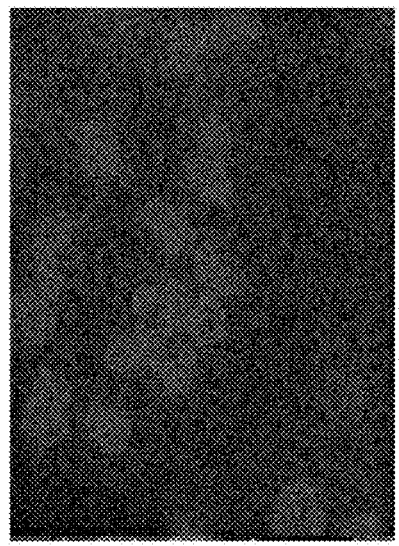
Figure 4G:
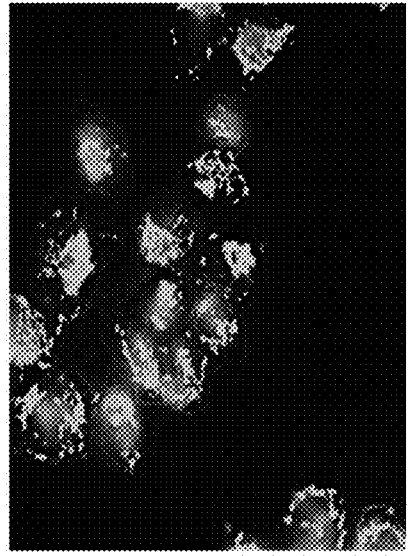
Figure 4H:
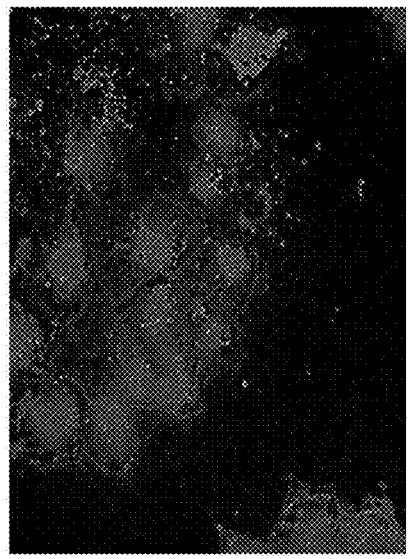
Figure 5A:
Figure 5B:
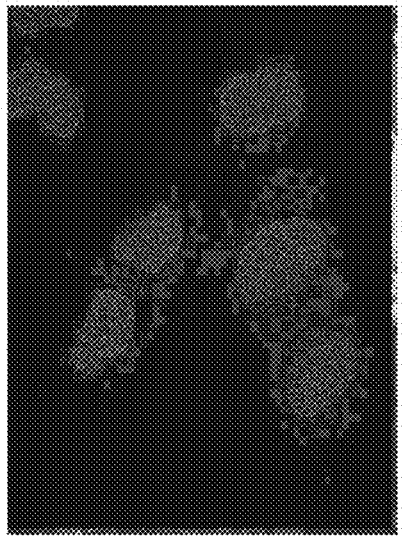
Figure 5C:
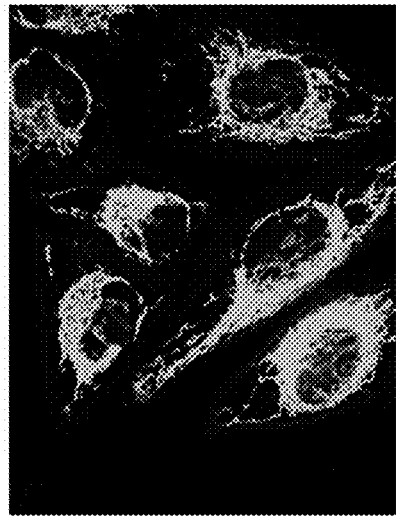
Figure 5D:
Figure 5E:
Figure 5F:
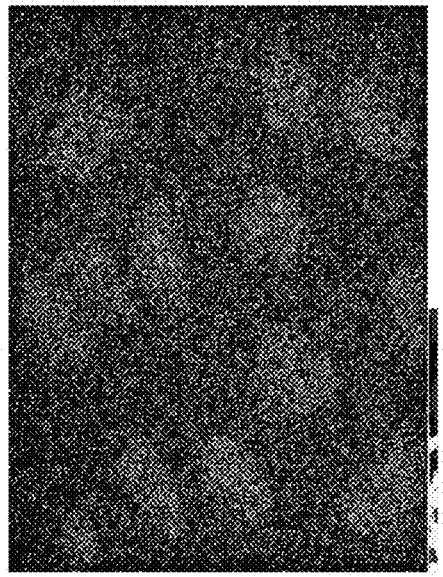
Figure 5G:
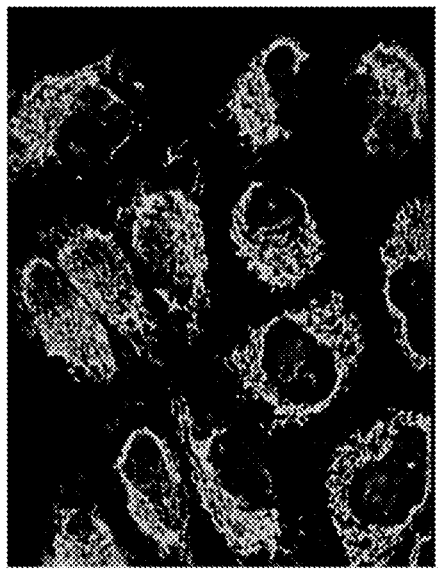
Figure 5H:
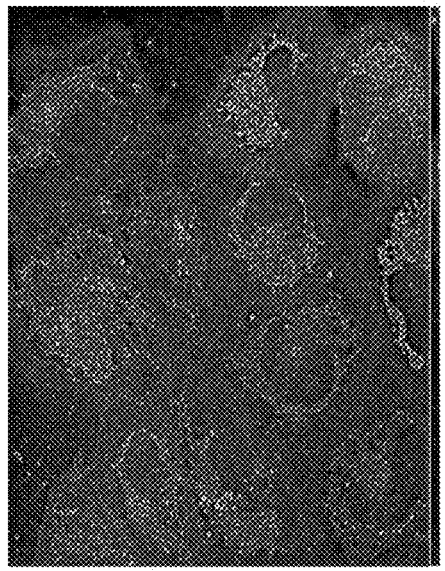

A 50-µmol portion of FMOC-r(F$_x$r)$_3$ was placed in a fritted 2.5-mL Torviq disposable syringe and swelled with 2 mL of anhydrous DMF for 1 h. The N-terminal FMOC group was removed by treating the resin with a solution of 25% 4-methylpiperidine in DMF (v/v) for a period of 30 min, followed by a 5×1.5 mL wash with DMF. A quantity of 200 µmol (90 mg) of [Pt(NH$_3$)$_2$(succac)]NO$_3$ was combined with 200 µmol (76 mg) of HATU (Oakwood Chemical). Immediately prior to coupling, solids were dissolved in 1.5 mL of a freshly prepared 10% DIPEA/DMF (v/v) solution, placed in the reaction vessel and shaken for 60 min. After the allotted time, the resulting solution was expelled from the syringe and the resin was washed with 5×1.5 mL of DMF. The resin was subsequently washed with 5×1.5 mL DCM and dried in vacuo for a period of ≥20 min prior to cleavage. Pt-MPP was cleaved from the resin by treating it with a TFA/water/triisopropylsilane 95/2.5/2.5% (v/v) solution for 90 min. The resulting crude peptide was precipitated with cold diethyl ether and purified by HPLC on the semi-preparative scale using a C$_{18}$ reverse-phase column (Zorbax SB-C$_{18}$, 9.4 mm×250 mm, 5 µm). A two-solvent system (A=0.1% TFA (v/v) in H$_2$O; B=0.1% TFA (v/v) in acetonitrile) was employed for purification according to the following protocol: isocratic flow, 10% B, 0-5 min; gradient, 10-50% B, 5-35 min. The flow-rate was kept constant at 3 mL min$^{-1}$ throughout the purification. Fractions from sequential runs containing Pt-MPP were pooled and lyophilized. The purity of the final product was assessed via analytical HPLC (Zorbax, SB-C$_{18}$, 4.6 mm×250 mm, 5 µm), according to the following protocol: after a 5 min isocratic wash (10% B), a linear gradient of 10-50% B was run over 30 min (35 min total) at a flow rate of 1 mL min$^{-1}$. 1 (retention time=22.1 min) was judged to be ≥95% pure based on the integrated chromatogram (FIG. 3). Observed peaks (calculated) in ESI-MS (m/z, amu): 1470.0 (1469.7) [M+H]$^+$; 735.4 (735.4) [M+2H]$^{2+}$; 484.8 (490.6) [M+3H]$^{3+}$. The parent [M+H]$^+$ peak (1470.0 amu) has a distinct platinum isotope pattern. $^{195}$Pt NMR (86 MHz, D$_2$O): δ −1591 ppm.

Synthesis of Pt-MPP(TAMRA), [Pt(succac)(NH$_3$)$_2$]-r(F$_x$r)$_3$K(5/6-carboxytetramethylrhodamine)-CONH$_2$ A 50-µmol portion of FMOC-r(F$_x$r)$_3$K(5(6)-TAMRA) was labeled with 200 µmol (90 mg) of [Pt(NH$_3$)$_2$(succac)]NO$_3$ using the procedure described above for the preparation of Pt-MPP. The purity of the two isomers (5 and 6) of Pt-MPP(TAMRA) were assessed via analytical HPLC (Zorbax, SB-C$_{18}$, 4.6 mm×250 mm, 5 µm), according to the same protocol as for Pt-MPP. The 5-isomer (retention time=26.5 min) was found to be ≥95% pure based on the integrated chromatogram (FIG. 3). The 6-isomer (retention time=25.7 min) was judged to be 94% pure based on the integrated chromatogram and not deemed sufficiently pure for further biological studies. Observed peaks for the 5-isomer of Pt-MPP(TAMRA) (calculated) in ESI-MS (m/z, amu): 1005.7 (1005.5) [M+H]$^+$; 670.8 (670.9) [M+2H]$^{2+}$; 503.3 (503.4) [M+3H]$^{3+}$. $^{195}$Pt NMR (86 MHz, D$_2$O): δ −1589 ppm.

X-Ray Crystallography

Single crystals of succinylacetone and [Pt(succac)(NH$_3$)$_2$](NO$_3$) were grown from hexanes/Et$_2$O and MeOH/Et$_2$O, respectively. Crystals were selected and mounted in n-paratone oil on a cryoloop, frozen under a 100 K KRYOFLEX nitrogen cold stream. A Bruker APEX CCD X-ray diffractometer with graphite-monochromated Mo—Kα radiation (λ=0.71073 Å) controlled by the APEX2 software package was utilized for data collection. Data were corrected for absorption with SADABS. The SHELXTL-97 software package was used to solve the structures with direct methods and further refine them against F$^2$. All non-hydrogen atoms were located on the difference map and refined anisotropically. The enol and carboxylic acid hydrogen atoms of succinylacetone were located on the difference map and semi-freely refined with constraints on the O—H distances (0.84 Å) and isotropic thermal displacement parameters of the hydrogen atoms (1.5 times that of the oxygen atoms to which they are attached). The carboxylic acid hydrogen atom of [Pt(succac)(NH$_3$)$_2$](NO$_3$) was also located and refined similarly. Other hydrogen atoms were placed at calculated positions and isotropic displacement parameters were constrained to be either 1.2 or 1.5 (terminal hydrogens) times those of the atoms to which they are bound.

Cell Culture

A2780 and A2780CP70 (ovarian cisplatin-sensitive and -resistant) cell lines were obtained from Fox Chase Cancer Center and cultured in RPMI-1640 medium supplemented with 10% fetal bovine serum (FBS) and 1% penicillin/ streptomycin. The cells were incubated in a humidified atmosphere containing 5% $CO_2$ at 37° C.

Cytotoxicity Assays

The colorimetric MTT assay was used to assess cytotoxicity. In a 96-well plate, 2000 cells per well were seeded in 100 μL growth medium and allowed to attach overnight. The growth media was then aspirated and replaced with 100 μL of growth medium containing varying concentrations of the platinum complexes. Six wells were used per concentration level. After 72 h, the platinum-containing media was aspirated and replaced with 200 μL of RPMI-1640 containing 0.67 mg/mL MTT. The cells were further incubated for 4 h. The MTT solution was removed, and the resulting purple formazan crystals were dissolved in 100 μL of 25:1 mixture of DMSO and aqueous ammonia. The absorbance was measured at 550 nm. The absorbance values were normalized to the Pt-free wells (100% cell viability) and are plotted versus platinum concentration. From the resulting curves, 50% growth inhibitory concentration ($IC_{50}$) values were determined by interpolation. These experiments were repeated at least three times, and the reported $IC_{50}$ values are the averages of these trials with the error estimated from the resulting standard deviations.

Cell Imaging Studies

A2780 and A2780CP70 cells were seeded in an imaging dish in 2 mL of growth medium. At ≈60% confluency, the cells were imaged. The growth media was swapped with premixed media containing 1 or 10 μM of the Pt-MPP (TAMRA) construct, and the cells were allowed to incubated with the dye for 1 h. The organelle dyes, Mito-tracker Green and Hoechst 33258, were added to the cells at 1.25-2.5 μM concentrations and allowed to incubate for 30 min. At the end of the incubation period, the media was aspirated, and the cells were washed with 3×1 mL PBS and submerged in 2 mL of dye-free DMEM for imaging. The imaging experiments were performed using a Zeiss Axiovert 200M inverted epifluorescence microscope equipped with an EM-CCD digital camera (Hamamatsu) and a MS200 XY Piezo Z stage (Applied Scientific Instruments). The light source was an X-Cite 120 metal-halide lamp (EXFO) and the fluorescence images were obtained using an oil-immersion objective at 63× magnification. The microscope was operated using Volocity software (Perkin-Elmer). Colocalization of the dyes was investigated with using the program ImageJ, using a previously described protocol (e.g., see French, A. P.; Mills, S.; Swarup, R.; Bennett, M. J.; Pridmore, T. P. *Nat. Protoc.* 2008, 3, 619-628).

Results and Discussion

Synthetic Strategy

Platinum conjugates can be categorized based on the attachment point of a peptide to the platinum agent, which occurs either at the non-leaving group ligand (e.g., amine) of a platinum(II) complex, leaving group ligand (e.g., carboxylate) of a platinum(II) complex, or through the axial ligands of platinum(IV) complex. By attaching a peptide to the non-leaving group ligands of a platinum anticancer agent, the reactivity of the platinum complex with DNA is generally altered, and the nature of the resulting DNA adducts and cellular responses are also presumably different from the parent drug. Different amine ligands, as in the case of oxaliplatin, give rise to platinum anticancer complexes with different spectra of activity and resistance profiles. Although desirable for the preparation of new platinum chemotherapeutics, these features are not preferred if one is seeking to investigate only how the change in cellular localization, directed by a conjugated peptide, affects the agent's biological activity. Thus, the MPP could either be attached to the leaving group ligand of a platinum(II) complex or to an axial ligand of a platinum(IV) complex. Platinum(IV) complexes generally need to be reduced to platinum(II) before binding to DNA or other cellular targets can occur. Two ligands are lost upon reduction. The commonly held notion that two axial ligands are exclusively eliminated upon reduction has been challenged by recent studies, which show that equatorial chloride ligand can also be lost. Hence, the reduced species is not necessary reflective of the parent platinum(II) agent. Furthermore, the reduction kinetics of platinum(IV) complexes are also dependent on the nature of the cell line used.

Because of the abovementioned complications for the other two approaches, it would be advantageous to use a leaving group ligand as an attachment point for the MPP. A ligand that contained both a β-diketonate unit for coordination to platinum(II) and a carboxylic acid or amine functionality for conjugation to a peptide via standard coupling chemistry was investigated. The compound succinylacetone, which can be prepared in one step from commercial reagents without the need for column chromatography, was employed in these studies.

Synthesis and Characterization of [Pt(succac)(NH$_3$)$_2$](NO$_3$)

The synthetic route utilized for the preparation of [Pt(succac)(NH$_3$)$_2$](NO$_3$) is as follows. As shown in Scheme 1, the diaqua analog of cisplatin was treated with the deprotonated succinylacetone to obtain the product. A previously reported workup protocol for this class of compounds, which calls for the evaporation of the aqueous solution, dissolution of the resulting residue in methanol, and precipitation of the product with diethyl ether, failed to give pure material. Instead, brown solids were typically obtained that did contain the desired product, as evidenced by ESI-MS, but of insufficient purity for further use and studies. The difficulty in isolating pure material may arise from the free carboxylic acid on the succinylacetone ligand, which can also coordinate to platinum(II), forming a wide array of undesired byproducts. To access pure compound, an alternative workup protocol was developed. A concentrated aqueous solution of the reaction mixture was acidified with HNO$_3$ to ensure full protonation of the carboxylic acid group. A series of precipitations was carried out using acetone, an acetone:ether mixture, and diethyl ether. The first two precipitations afforded oily orange-brown residues and white slightly turbid supernatant. Pure compound was isolated from the supernatant upon the addition of further volumes of diethyl ether as a white solid.

Scheme 1.

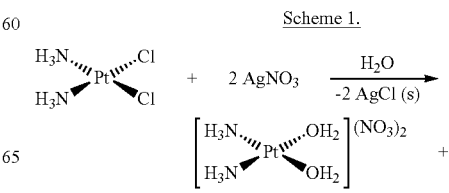

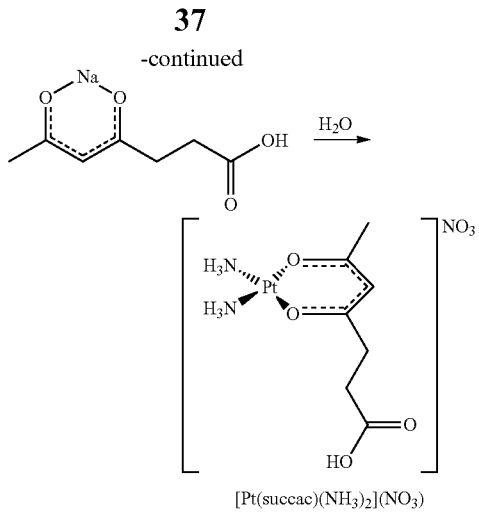

[Pt(succac)(NH$_3$)$_2$](NO$_3$)

Elemental analysis and ESI-MS were in accord with the proposed formula. Furthermore, multinuclear NMR spectroscopy established the purity and identity of the compound. The $^1$H and $^{13}$C NMR spectra display all expected resonances for the proposed structure of this compound. Notably, the NH$_3$ protons of the coordinated ammine ligands, which readily exchange with protic or deuteric solvents, could be observed in MeOD-d$_4$ as a broad feature at 4.44 ppm if spectra were acquired within half an hour of preparation of the NMR sample. The observed chemical shift of 4.44 ppm is in the expected region for NH$_3$ protons coordinated to platinum(II). The $^{195}$Pt NMR spectrum of [Pt(succac)(NH$_3$)$_2$](NO$_3$) shows a single broad peak centered at −1570 ppm. The free carboxylic acid of [Pt(succac)(NH$_3$)$_2$](NO$_3$) may have a subtle effect on the coordination sphere of the platinum center, possibly by an intramolecular hydrogen-bond with a coordinated ammine ligand.

Succinylacetone and [Pt(succac)(NH$_3$)$_2$](NO$_3$) were both characterized crystallographically. Succinylacetone crystallizes as its enol tautomer, as verified the disparate C—O bond distances, which are indicative of one single C—O bond and one double C=O bond. Furthermore, the hydrogen atom of the enol could be definitively located on the difference map. The crystal structure of [Pt(succac)(NH$_3$)$_2$](NO$_3$) confirmed the coordination of the succac ligand through the β-diketonate unit rather than the carboxylic acid. The delocalized nature of the β-diketonate ligand was ascertained from the similar C—O and C—C bond distances that comprise the six-member chelate ring.

Preparation of Pt-MPP and Pt-MPP(TAMRA)

The Pt-MPP conjugates were prepared directly on a solid-phase resin. The resins, which contained the MPP and the TAMRA-labeled MPP attached via the C-terminus, were soaked in a DMF solution containing an excess of [Pt(succac)(NH$_3$)$_2$](NO$_3$) preactivated with the coupling reagent HATU. The resin was then washed, and the peptides were cleaved form the solid-phase support with 95% TFA. Preparative HPLC allowed isolation of the expected Pt-conjugates in greater than 95% purity. The TAMRA-labeled peptide was provided as a mixture of isomers, which differed in the attachment point of the peptide to the bottom ring of the TAMRA dye (5 or 6 position). Only one of the isomers was successfully isolated with >95% purity. The final constructs, Pt-MPP and Pt-MPP(TAMRA), are shown in FIG. 3.

The conjugates were characterized by ESI-MS and NMR spectroscopy. The mass spectra displayed ink peaks of the +1, +2, and +3 ions, which were all marked by isotopic fine structure characteristic of the six naturally abundant isotopes of platinum. $^{195}$Pt NMR spectra in D$_2$O could be obtained for both constructs. Both species have single signal near −1590 ppm. These values are identical to that of [Pt(acac)(NH$_3$)$_2$](SO$_4$)$_{0.5}$, which resonated at −1593 ppm. Hence, the diammine(β-diketonate) coordination sphere of the platinum atoms was retained in the peptide-conjugates, even after cleavage from the resin with 95% TFA. $^1$H NMR spectra were also obtained. Diagnostic peaks for the proton at the γ-position of the β-diketonate ligand were found at 5.68 and 5.61 ppm as sharp singlets for Pt-MPP and Pt-MPP(TAMRA), respectively. Furthermore, the CH$_3$ resonances of the succinylacetone ligand were located at 1.88 and 1.83 ppm for the labeled and unlabeled constructs. The aromatic region of the $^1$H NMR spectrum of Pt-MPP(TAMRA) displayed all the expected signals for the TAMRA dye. The singlet of H$_f$ in CD$_3$OD resonates at 7.97 ppm for the 6 isomer of carboxytetramethylrhodamine and at 8.73 ppm for the 5 isomer. Hence, the construct contains isomerically pure 5 isomer as drawn because this resonance is observed at 8.63 ppm.

Cytotoxicity Studies

For cytotoxicity studies, the cisplatin-sensitive and -resistant ovarian cancer cell lines A2780 and A2780CP70 were used. In addition to testing cisplatin and Pt-MPP, [Pt(acac)(NH$_3$)$_2$](SO$_4$)$_{0.5}$ and [Pt(succac)(NH$_3$)$_2$](NO$_3$) were also investigated. These two complexes were used as peptide-free controls. Their ligand substitution kinetics are expected to be more comparable to that of Pt-MPP because the three constructs all employ similar O-diketonate leaving group ligands. The results of these assays using a 72 h incubation period are summarized in Table 1, where IC$_{50}$ values were collected. In Table 1, resistance factors (R.F.'s), which are defined as the ratios of IC$_{50}$ values of the resistant to sensitive cell lines, are given as well.

TABLE 1

IC$_{50}$ Values and Resistance Factors (R.F.'s)
Measured After a 72 h Incubation Period

| | IC$_{50}$ (μM)$^a$ | | |
|---|---|---|---|
| Compound | A2780 | A2780CP70 | R.F.$^b$ |
| cisplatin | 0.60 ± 0.08 | 5.2 ± 1.4 | 8.7 ± 2.6 |
| Oxaliplatin | 0.25 ± 0 μM* | 1.0 ± 0.1 μM* | 4.1 ± 0.4 |
| Pt-MPP (also referred to in Example 1 as [Pt(NH$_3$)$_2$(succac-(F$_x$r)$_3$)]) | 7.5 ± 0.3 | 5.0 ± 1.4 | 0.7 ± 0.2 |

TABLE 1-continued

IC$_{50}$ Values and Resistance Factors (R.F.'s)
Measured After a 72 h Incubation Period

| | IC$_{50}$ (μM)$^a$ | | |
|---|---|---|---|
| Compound | A2780 | A2780CP70 | R.F.$^b$ |
| [Pt(DACH)(succac-(F$_x$r)$_3$)] | 3.9 ± 0.6 μM | 15.9 ± 7.0 μM | 4.1 ± 0.9 |
| [Pt(DACH)(succac)](NO$_3$) | 18.5 ± 1.6 μM* | 85.3 ± 3.1 μM* | 4.6 ± 0.6 |
| [Pt(acac)(NH$_3$)$_2$](SO$_4$)$_{0.5}$ | 13.9 ± 1.9 | 122 ± 10. | 8.8 ± 1.4 |
| [Pt(succac)(NH$_3$)$_2$](NO$_3$) | 220 ± 40 | 855 ± 35 | 3.9 ± 0.7 |

$^a$Values are the average from at least three independent experiments and reported errors are the standard deviations unless * wherein value is the average of two independent experiments.
$^b$R.F. = resistance factor, defined as IC$_{50}$(resistant)/IC$_{50}$(sensitive)

Cisplatin effectively kills A2780 cells at submicromolar concentration levels. In the resistant line, however, the IC$_{50}$ value increases by almost one order of magnitude. [Pt(acac)(NH$_3$)$_2$](SO$_4$)$_{0.5}$ is less effective than cisplatin with IC$_{50}$ values in both cell lines that are approximately 20 times larger. The least cytotoxic compound tested is [Pt(succac)(NH$_3$)$_2$](NO$_3$) as indicated by its IC$_{50}$ values, which are greater than 200 μM in both cell lines. In the sensitive cell line, the Pt-MPP is less cytotoxic than cisplatin, but more so than [Pt(acac)(NH$_3$)$_2$](SO$_4$)$_{0.5}$. In the resistant cell line, however, Pt-MPP is equitoxic with cisplatin. Additionally, the resistance factor of this construct is 0.7±0.2, thus indicating that it avoids traditional cisplatin resistance mechanisms in this cell line.

Cell Imaging Studies

Imaging studies of the TAMRA-labeled Pt-MPP were carried out in both resistant and sensitive A2780 cell lines. Both 1 and 10 μM incubation concentrations were used for these studies. Representative images for both cell lines and concentrations are shown in FIGS. 4 and 5, and Pearson's correlation coefficients, describing the degree of colocalization of Pt-MPP(TAMRA) with the organelle dyes, are collected in Table 2.

In FIG. 4: Images of A2780 cells treated with 1 μM Pt-MPP(TAMRA) for 1 h visualized by (A) DIC, (B) blue channel (Hoechst 33258), (C) green channel (Mito-tracker green), and (D) the red channel (TAMRA); and images of A2780 cells treated with 10 μM Pt-MPP(TAMRA) for 1 h visualized by (E) DIC, (F) blue channel (Hoechst 33258), (G) green channel (Mito-tracker green), and (H) the red channel (TAMRA).

In FIG. 5: Images of A2780CP70 cells treated with 1 μM Pt-MPP(TAMRA) for 1 h visualized by (A) DIC, (B) blue channel (Hoechst 33258), (C) green channel (Mito-tracker green), and (D) the red channel (TAMRA); and images of A2780CP70 cells treated with 10 μM Pt-MPP(TAMRA) for 1 h visualized by (E) DIC, (F) blue channel (Hoechst 33258), (G) green channel (Mito-tracker green), and (H) the red channel (TAMRA).

TABLE 2

Pearson's Correlation Coefficients (PCC) for Colocalization
of Pt-MPP(TAMRA) and the Organelle Dyes

| Cell Line, Concentration | Mitochondrial PCC | Nuclear PCC |
|---|---|---|
| A2780, 1 μM | 0.36 ± 0.08 | −0.03 ± 0.04 |
| A2780, 10 μM | 0.45 ± 0.08 | 0.0 ± 0.03 |
| A2780CP70, 1 μM | 0.40 ± 0.18 | 0.03 ± 0.06 |
| A2780CP70, 10 μM | 0.53 ± 0.13 | 0.0 ± 0.01 |

For both cell lines, Pt-MPP(TAMRA) showed moderately good localization to the mitochondria. The extent of the localization appears to be dependent on the concentration of construct with better mitochondrial localization observed at the 10 μM concentration level. These results indicate that Pt-MPP(TAMRA) does not go to the nucleus; Pearson's correlation coefficients for overlap with the nuclear stain are all effectively 0. Some punctate staining was observed in the red channel. Several of these intense, sharp signals occur in extracellular locations. The precise origin of these punctate features remains uncertain, but may arise from precipitation of the peptide, possibly due to aggregation. In the absence of these signals, the Pearon's correlation coefficients for mitochonodrial localization may increase.

Cellular resistance to cisplatin can arise at one or many different points during the drug's mechanisms of action. Pre-target resistance can occur as a result of either decreased cellular uptake or increased intracellular sequestration by off-target nucleophiles such as glutathione. When cisplatin locates and binds to DNA, on-target resistance pathways, which includes increased repair of platinum-DNA adducts, can take effect. Post-target pathways occur if the cell fails to trigger apoptosis or other cell death pathways in response to DNA damage induced by cisplatin. The mechanisms of cisplatin resistance in the A2780CP70 cell line have been the subject of many investigations. From these previous reports, it appears that many of the abovementioned factors contribute to cisplatin resistance in this cell line. Post-target resistance, however, may not be important because A2780CP70 cells can activate the apoptotic cell death pathway. Additionally, cellular uptake does not appear to be responsible for this resistance either because at short exposure times (1-4 h) cisplatin is taken up to almost equal extents in both cell lines. On the otherhand, the resistant cell line does exhibit increased glutathione levels in comparison to the sensitive line, which suggests that sequestration of the active drug by these thiols could be a contributing factor to the resistance. Further studies found that the resistant cell line can more efficiently remove Pt-DNA crosslinks, and that resistance can be overcome by inhibiting the nucleotide excision repair pathway.

Given these known resistance mechanisms in A2780CP70 cells, the question naturally arises as to how Pt-MPP can circumvent them whereas the other platinum agents tested in this example did not. Because both cisplatin and the Pt-MPP constructs contain the same non-leaving group unit, [Pt(NH$_3$)$_2$], the nature of the resulting DNA adducts and the cellular response is likely to be similar. Hence, an on-target circumvention of resistance may be ruled out. Additionally, the similar structure of the compounds comprising MPP to that of [Pt(acac)(NH$_3$)$_2$](SO$_4$)$_{0.5}$ suggests that both species may be equally susceptible to deactivation by glutathione.

Therefore, a difference in this off-target mechanism of resistance is most likely not operable. Essentially two other possibilities exist; either the Pt-MPP construct exhibits enhanced cellular uptake in the resistant cell line and/or it is hitting a completely different target which is not susceptible to the same resistance mechanisms as the conventional platinum target, nuclear DNA. The cell localization studies using the TAMRA-labeled conjugate indicate that the construct localizes to the mitochondria to a much higher extent than the nucleus. This result suggests that the platinum may be avoiding traditional resistance pathways by targeting the mitochondria, however, assumes that the TAMRA dye and additional lysine residue do not significantly alter the cellular distribution properties of the original construct.

In summary, the conjugation of platinum anticancer compound to an MPP formed an agent that was able to circumvent traditional cisplatin-resistance mechanisms.

Whereas several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:
1. A compound having the structure:

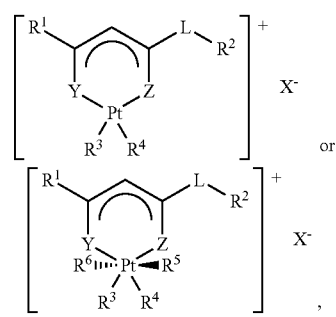

wherein:
R$^1$ is selected from the group consisting of alkyl optionally substituted, heteroalkyl optionally substituted, and aryl optionally substituted;

R² is a targeting moiety, wherein R² is a protein, a peptide, a nucleic acid, a nucleic acid analog, a carbohydrate, or a small molecule;

R³ and R⁴ are independently selected from the group consisting of ammonia, an optionally substituted heterocycle including at least one nitrogen, and an optionally substituted amine, or R³ and R⁴ can be joined together to form a bidentate ligand;

R⁵ and R⁶ are independently selected from the group consisting of hydroxyl, alkoxy, aryloxy, and acyloxy, each optionally substituted;

L is a linking group;

Z and Y are independently selected from the group consisting of O and S; and

X⁻ is a counterion.

2. The compound of claim 1, wherein L comprises the structure —(CH₂)—(C=O)—, —(CH₂)ₙ(C=O)NH—, —[(CH₂)ₘO]ₙ(C=O)—, or —[(CH₂)ₘO]ₙ(C=O)NH—, wherein n is an integer.

3. The compound of claim 1, wherein at least one of R³ and R⁴ is NH₃.

4. The compound of claim 1, wherein each of R³ and R⁴ is NH₃.

5. The compound of claim 1, wherein R³ and R⁴ are independently selected from the group consisting of ammonia and an optionally substituted amine, and are not joined together to form a bidentate ligand.

6. The compound of claim 1, wherein Z is O and Y is S.

7. The compound of claim 1, wherein Z is S and Y is O.

8. The compound of claim 1, wherein each of Z and Y is O.

9. The compound of claim 1, wherein each of Z and Y is S.

10. A method for treating a subject having a cancer, comprising:
administering a therapeutically-effective amount of a compound as in claim 5 to a subject having a cancer.

11. A method, comprising:
promoting the inhibition or treatment of a cancer in a subject susceptible to or exhibiting symptoms of a cancer via administration to the patient of a composition comprising a compound as in claim 1.

12. A kit for treatment of a cancer, comprising:
a composition comprising a compound as in claim 1; and
instructions for use of the composition for treatment of a cancer.

13. A pharmaceutical composition, comprising:
a compound as in claim 1; and
one or more pharmaceutically acceptable carriers, additives, and/or diluents.

14. The compound of claim 1, wherein the peptide comprises a cell-penetrating peptide or a mitochondria-penetrating peptide.

15. The compound of claim 14, wherein the cell-penetrating peptide is one or more of Tat peptide, oligoarginine (r9), oligolysine (k9), and penetratin.

16. The compound of claim 14, wherein the mitochondria-penetrating peptide is one or more of (FₓR)ᵦ wherein Fₓ and r are cyclohexylalanine and d-arginine, respectively, and b is an integer greater than 1.

17. The compound of claim 1, wherein the targeting moiety comprises a label.

18. The compound of claim 17, wherein the label is a fluorescent label.

19. The compound of claim 1, wherein the targeting moiety comprises a terminating group.

20. The compound of claim 1, wherein the compound has the structure:

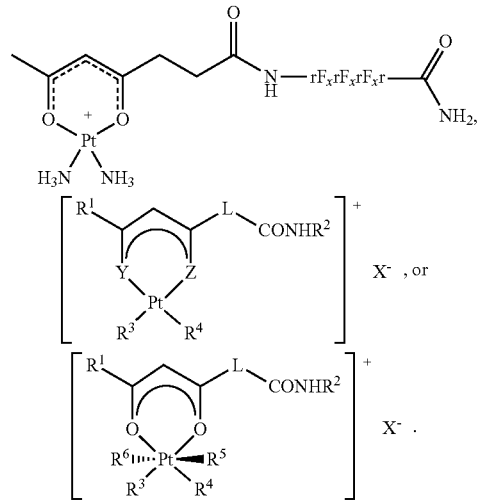

21. A compound having the structure:

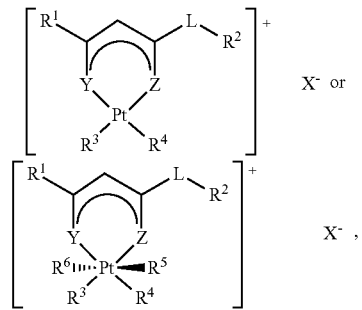

wherein:

R¹ is selected from the group consisting of alkyl optionally substituted, heteroalkyl optionally substituted, and aryl optionally substituted;

R² is a targeting moiety;

R³ and R⁴ are independently selected from the group consisting of ammonia, an optionally substituted heterocycle including at least one nitrogen, and an optionally substituted amine, or R³ and R⁴ can be joined together to form a bidentate ligand;

R⁵ and R⁶ are independently selected from the group consisting of hydroxyl, alkoxy, aryloxy, and acyloxy, each optionally substituted;

L comprises the structure —(CH₂)ₙ(C=O)—, —(CH₂)ₙ(C=O)NH—, —[(CH₂)ₘO]ₙ(C=O)— or —[(CH₂)ₘO]ₙ(C=O)NH—, wherein each m and n is an integer;

Z and Y are independently selected from the group consisting of O and S; and

X⁻ is a counterion.

22. The compound of claim 21, wherein R² comprises at least one of a protein, a peptide, a nucleic acid, a nucleic acid analog, a carbohydrate, a small molecule, an antibody, a nanoparticle, a sugar, and a polymer.

23. The compound of claim 22, wherein the targeting moiety comprises a label or a terminating group.

24. A method, comprising:
promoting the inhibition or treatment of a cancer in a subject susceptible to or exhibiting symptoms of a cancer via administration to the patient of a composition comprising a compound as in claim 21.

25. The compound of claim 1, wherein the targeting moiety comprises a label or a terminating group.

26. A compound having the structure:

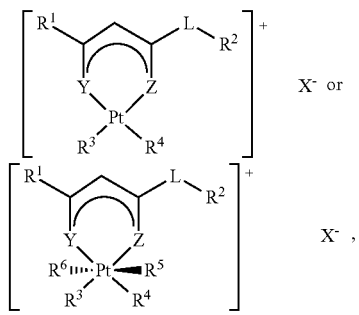

X⁻ or

X⁻, wherein:

$R^1$ is selected from the group consisting of alkyl optionally substituted, heteroalkyl optionally substituted, and aryl optionally substituted;

$R^2$ is a targeting moiety;

$R^3$ and $R^4$ are independently selected from the group consisting of ammonia, an optionally substituted heterocycle including at least one nitrogen, and an optionally substituted amine, or $R^3$ and $R^4$ can be joined together to form a bidentate ligand;

$R^5$ and $R^6$ are independently selected from the group consisting of hydroxyl, alkoxy, aryloxy, and acyloxy, each optionally substituted;

L is a linking group;

Z and Y are independently selected from the group consisting of O and S, wherein Z is O and Y is S or wherein Z is S and Y is O; and $X^-$ is a counterion.

27. The compound of claim 26, wherein $R^2$ comprises at least one of a protein, a peptide, a nucleic acid, a nucleic acid analog, a carbohydrate, a small molecule, an antibody, a nanoparticle, a sugar, and a polymer.

28. The compound of claim 26, wherein the targeting moiety comprises a label or a terminating group.

29. A method, comprising:
promoting the inhibition or treatment of a cancer in a subject susceptible to or exhibiting symptoms of a cancer via administration to the patient of a composition comprising a compound as in claim 26.

* * * * *

UNITED STATES PATENT AND TRADEMARK OFFICE
CERTIFICATE OF CORRECTION

PATENT NO.         : 9,593,139 B2                        Page 1 of 1
APPLICATION NO.    : 14/245360
DATED              : March 14, 2017
INVENTOR(S)        : Stephen J. Lippard et al.

It is certified that error appears in the above-identified patent and that said Letters Patent is hereby corrected as shown below:

In the Claims

In Claim 2, at Column 43, Lines 18-19, please replace:
"--$(CH_2)$--$(C=O)$--, --$(CH_2)_n(C=O)NH$--, --$[(CH_2)_mO]_n(C=O)$--, or --$[(CH_2)_mO]_n(C=O)NH$--,"
With:
"-$(CH_2)_n(C=O)$-, -$(CH_2)_n(C=O)NH$-, -$[(CH_2)_mO]_n(C=O)$-, or -$[(CH_2)_mO]_n(C=O)NH$-,"

Signed and Sealed this
Thirtieth Day of January, 2018

Joseph Matal
*Performing the Functions and Duties of the
Under Secretary of Commerce for Intellectual Property and
Director of the United States Patent and Trademark Office*